US008337822B2

(12) United States Patent
Brun

(10) Patent No.: US 8,337,822 B2
(45) Date of Patent: *Dec. 25, 2012

(54) USE OF A POLYSILOXANE/POLYUREA BLOCK COPOLYMER FOR THE TREATMENT OF KERATINOUS FIBERS

(75) Inventor: Gaëlle Brun, Paris (FR)

(73) Assignee: L'Oreal, Paris (FR)

( * ) Notice: Subject to any disclaimer, the term of this patent is extended or adjusted under 35 U.S.C. 154(b) by 1232 days.

This patent is subject to a terminal disclaimer.

(21) Appl. No.: 11/976,555

(22) Filed: Oct. 25, 2007

(65) Prior Publication Data

US 2008/0171010 A1 Jul. 17, 2008

Related U.S. Application Data

(60) Provisional application No. 60/861,039, filed on Nov. 27, 2006.

(30) Foreign Application Priority Data

Oct. 25, 2006 (FR) ...................... 06 54534

(51) Int. Cl.
*A61Q 5/06* (2006.01)
(52) U.S. Cl. .................................... 424/70.12
(58) Field of Classification Search ........................ None
See application file for complete search history.

(56) References Cited

U.S. PATENT DOCUMENTS

| 6,395,265 | B1 | 5/2002 | Mougin et al. | |
|---|---|---|---|---|
| 6,410,004 | B1 | 6/2002 | Kim et al. | |
| 6,626,962 | B1 * | 9/2003 | Lang et al. | 8/405 |
| 7,063,834 | B2 | 6/2006 | Mougin et al. | |
| 7,799,093 | B2 * | 9/2010 | Brun et al. | 8/405 |
| 7,806,941 | B2 * | 10/2010 | Brun et al. | 8/405 |
| 2002/0150546 | A1 | 10/2002 | Mougin et al. | |
| 2002/0155079 | A1 | 10/2002 | Kim et al. | |
| 2004/0210024 | A1 * | 10/2004 | Schafer et al. | 528/44 |
| 2005/0232882 | A1 * | 10/2005 | Bebot et al. | 424/70.1 |

FOREIGN PATENT DOCUMENTS

| DE | 10 2005 017 277 A1 | 4/2006 |
|---|---|---|
| EP | 1 035 144 A2 | 9/2000 |
| EP | 1 672 006 A1 | 6/2006 |
| WO | WO 97/25021 | 7/1997 |

OTHER PUBLICATIONS

French Search Report for FR 0654534, dated May 11, 2007.
English language abstract of DE 10 2005 017 277 A1, Apr. 20, 2006.
English language abstract of EP 1 672 006 A1, Jun. 21, 2006.

* cited by examiner

*Primary Examiner* — Jyothsna Venkat
(74) *Attorney, Agent, or Firm* — O'Brien Jones, PLLC

(57) ABSTRACT

The present disclosure relates to a treatment of the hair, which is resistant to shampooing operations, wherein the individual hairs are coated with a cosmetic composition comprising a polysiloxane/polyurea block copolymer wherein at least one volatile nonsilicone organic solvent and at least one silicone compound exhibit a viscosity of less than 100 cSt.

14 Claims, No Drawings

USE OF A POLYSILOXANE/POLYUREA BLOCK COPOLYMER FOR THE TREATMENT OF KERATINOUS FIBERS

This application claims benefit of U.S. Provisional Application No. 60/861,039, filed Nov. 27, 2006, the contents of which are incorporated herein by reference. This application also claims benefit of priority under 35 U.S.C. §119 to French Patent Application 0654534, filed Oct. 25, 2006, the contents of which are also incorporated herein by reference.

The present disclosure relates to the use for the treatment of keratinous fibers, such as the hair, for example, the coating of the individual hairs, of a cosmetic composition comprising a polysiloxane/polyurea block copolymer.

The hair is generally damaged and embrittled by the action of external atmospheric agents, such as light and bad weather, and by mechanical or chemical treatments, such as brushing, combing, bleaching, perming and/or dyeing. The result of this damage is that the hair may be difficult to manage, for example, it may be difficult to disentangle or to style and heads of hair, even densely populated heads of hair, may retain with difficulty a style which is attractive in appearance due to the fact that the hair lacks vigor, volume and liveliness.

Thus, in order to overcome this, it is now common practice to use styling products which make it possible to condition the hair by providing it, e.g., with body, bulk or volume.

These styling products are generally hair cosmetic compositions comprising one or more polymers which exhibit a high affinity for the individual hairs and which generally have the role of forming a film at their surface for the purpose of modifying their surface properties, for instance, in order to condition them.

One disadvantage related to the use of these hair compositions lies in the fact that the cosmetic effects conferred by such compositions have a tendency to disappear, even after the first shampooing.

In order to overcome this disadvantage, it is possible to envisage increasing the persistence of the deposited layer of polymers by directly carrying out a radical polymerization of certain monomers on the individual hairs. However, the treatments used thus far tend to result in damage to the fiber and the hair in such a manner that the hair thus treated may be generally difficult to disentangle.

Furthermore, it is known practice in the art to carry out coatings of individual hairs starting from a composition comprising an electrophilic monomer of cyanoacrylate type, for example, in French Patent Application No. 2 833 489. Such a composition makes it possible to obtain individual hairs which are perfectly coated and nongreasy. However, the coating obtained is not entirely satisfactory in the face of external agents, such as washing and perspiration. Also, the coating obtained is often sensitive to fatty substances, such as sebum.

European Patent Application No. 1 266 647 and International Patent Application No. WO 2005/060922 describe compositions intended for making up the lips, eyelashes or complexion which comprise a polysiloxane copolymer comprising at least one unit capable of forming hydrogen bonds. Mention is made, as an example of units capable of forming hydrogen bonds of polyureas. However, these documents do not envisage the use in the hair field of such a composition for the coating of individual hairs.

Accordingly, there is a need in the art for method for the treatment of keratinous fibers, such as the hair, which makes it possible to obtain coatings which are resistant to shampooing operations and towards various attacks to which the hair may be subjected, for instance, blow-drying operations and/or perspiration, while resisting fatty substances, such as sebum, and while retaining the integrity of the keratinous fibers.

Thus, the present disclosure, in one embodiment, relates to a method for treating keratinous fibers, such as hair, by applying to the fibers an anhydrous cosmetic composition comprising at least one nonionic polysiloxane/polyurea block copolymer.

Another aspect of the present disclosure is a cosmetic composition comprising at least one nonionic polysiloxane/polyurea block copolymer, at least one volatile nonsilicone organic solvent and at least one silicone compound exhibiting a viscosity of less than 100 mm$^2$/s (100 centistokes) at 25° C.

Using such a copolymer, coatings are obtained on keratinous fibers which make it possible to obtain volume, bulk and/or body of the hair in a way which is resistant to shampooing operations while retaining the physical qualities of the keratinous fibers. Such a coating is, for example, resistant to the external attacks to which the hair may be subjected, such as blow drying and/or perspiration.

The coating thus formed exists in the form of a homogeneous and smooth deposited layer which generally has excellent adhesion to individual hairs. The present inventors have discovered that the hairs remained completely separate and could be styled without a problem and that the styling properties introduced into the fiber were resistant to shampooing operations.

In at least one embodiment of the present disclosure, the copolymer is a nonionic polysiloxane/polyurea copolymer, i.e., it does not comprise ionized or ionizable groups.

As used herein, "block copolymer" is understood to mean a copolymer composed of at least two separate sequences of each of the polymers constituting the copolymer in the backbone of the copolymer, for example, the copolymer of the invention comprises at least one sequence (or block) of polysiloxane and at least one sequence (block) of polyurea in the backbone of the copolymer.

The copolymer of the present disclosure may additionally comprise other blocks of different units, for example, polysiloxane/polyurea/polyurethane block terpolymers.

According to at least one embodiment, the copolymer may be present in the cosmetic composition in an amount greater than 5% by weight of polysiloxane. According to another embodiment, the amount of polysiloxane is predominant in the copolymer, for instance, greater than 90% by weight, with respect to the total weight of the copolymer.

As disclosed herein, the copolymer may comprise at least one siloxane block and at least one polyurea block.

According to the present disclosure, the copolymer can correspond to formula (I):

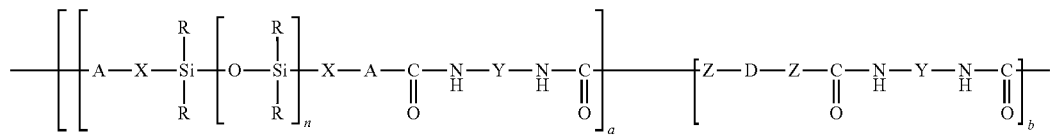

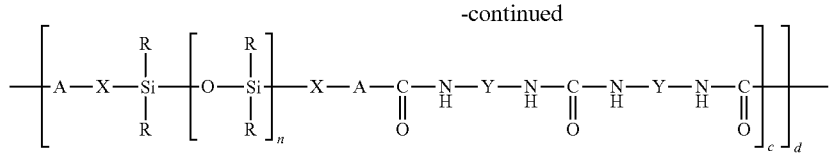

wherein:
R is a monovalent $C_1$-$C_{20}$ hydrocarbon radical, that may be substituted, for example, with fluorine or chlorine,
X is a $C_1$-$C_{20}$ alkylene radical, wherein nonneighboring methylene units can be replaced by —O— radicals,
A is chosen from an oxygen atom and an amino radical —NR'—,
Z is chosen from an oxygen atom and an amino radical —NR'—,
R' is chosen from a hydrogen atom and a $C_1$-$C_{10}$ alkyl radical,
Y is a divalent $C_1$-$C_{20}$ hydrocarbon radical, that may be substituted, for example, with fluorine or chlorine,
D is an $C_1$-$C_{700}$ alkylene radical, that may be substituted, for example, with fluorine, chlorine, $C_1$-$C_6$ alkyl or $C_1$-$C_6$ alkyl ester, wherein nonneighboring methylene units can be replaced by —O—, —COO—, —OCO— or —OCOO— radicals,
n is a number ranging from 1 to 4000,
a is a number of at least 1,
b is a number ranging from 0 to 40,
c is a number ranging from 0 to 30, and
d is a number greater than 0,
wherein in at least one embodiment, A is, in at least one of the units (a), an NH radical.

In at least one embodiment, R is chosen from a monovalent $C_1$-$C_6$ hydrocarbon radical, for example, methyl, ethyl, vinyl and phenyl. According to another embodiment, R is an unsubstituted alkyl radical.

In at least one embodiment, X is a $C_2$-$C_{10}$ alkylene radical. According to another embodiment, the alkylene radical X is not interrupted.

According to at least one embodiment, the A group in all the units (b) and (c), when they are present, is NH.

According to another embodiment, all the A groups are NH radicals.

According to at least one embodiment, Z is an oxygen atom or an NH radical.

According to another embodiment, Y is a $C_3$-$C_{13}$ hydrocarbon radical that may, in at least one embodiment, be unsubstituted. In yet another embodiment, Y is an aralkylene or alkylene radical which is linear or cyclic.

In at least one embodiment, D is an alkylene radical having at least 2, for example, at least 4, carbon atoms, and at most 12 carbon atoms.

According to another embodiment, D is a polyoxyalkylene radical, for example, a polyoxyethylene or polyoxypropylene radical, having at least 20, for example at least 100, carbon atoms, and at most 800, for example, at most 200, carbon atoms.

In at least one embodiment, the radical D is unsubstituted.

In at least one embodiment, n is a number of at least 3, for example at least 25, an of no more than 800, for example, no more than 400, or no more than 250.

In another embodiment, a is a number greater than 50.

When b is other than 0, b is a number of at most 500, for example, at most 25.

In at least one embodiment, c is a number of at most 10, for instance, at most 5.

The copolymers of the present disclosure can be obtained according to the polymerization processes described in U.S. Patent Application Publication No. 2004/0254325 or International Application No. WO 03/014194.

The copolymer can thus be obtained by a two-stage process, such that:
in a first stage, a silazane of formula (2) or (2'):

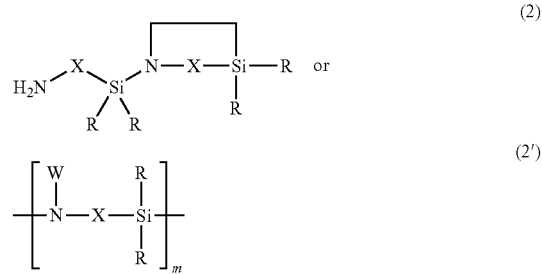

wherein W is chosen from a hydrogen atom, a substituted or unsubstituted hydrocarbon radical comprising, in one embodiment, from 1 to 20 carbon atoms, and an $R_2Si$—X—$NH_2$ radical, and m is a number ranging from 1 to 4000.
is reacted with an organic silicon compound of formula (3):

$$(HO)(R_2SiO)_{n-1}[H] \qquad (3)$$

in order to obtain an aminoalkylpolydiorganosiloxane of formula (4):

$$H_2N-X-[SiR_2O]_nSiR_2-X-NH_2 \qquad (4)$$

in a second stage, the aminoalkylpolydiorganosiloxane of formula (4) is polymerized with a diisocyanate of formula (5):

$$OCN-Y-NCO \qquad (5)$$

Generally, in a first stage, the silazanes of formula (2) or (2') and the reactants comprising silanol groups are employed in equimolar ratios.

For preparation of very pure silicones comprising a bisaminoalkyl ending of formula (4), use may be made, for example, of a small excess of the silazane compound of formula (2) or (2'), which can subsequently be removed in a simple additional process stage, such as, the addition of small amounts of water.

If b is at least 1, use may be made, during the second stage, of up to 95% by weight, on the basis of all the components employed, of chain-extending agents which are chosen from diamines, hydroxyl compounds masked by an isocyanate, dihydroxyl compounds or their mixtures. In at least one embodiment of the present disclosure, the chain-extending agents may exhibit formula (6):

$$HZ-D-ZH \qquad (6)$$

wherein D and Z exhibit the above meanings. If Z has the meaning O, the chain-extending agent of formula (6) can also be reacted, before the reaction in the second stage, with the diisocyanate of formula (5). If appropriate, water can be employed as chain-extending agent.

Non-limiting examples of diisocyanates of formula (5) that may be used in the present disclosure include formulaaliphatic compounds, such as isophorone diisocyanate, 1,6-hexamethylene diisocyanate, 1,4-tetramethylene diisocyanate and 4,4'-methylenedicyclohexyl diisocyanate, or aromatic compounds, such as 4,4'-methylenediphenyl diisocyanate, 2,4-toluene diisocyanate, 2,5-toluene diisocyanate, 2,6-toluene diisocyanate, m-phenylene diisocyanate, p-phenylene diisocyanate, m-xylene diisocyanate, tetramethyl-m-xylene diisocyanate or mixtures of these isocyanates. A non-limiting example of a commercially available compound is a diisocyanate of the Desmodur® series (H, I, M, T, W) from Bayer AG, Germany. In at least one embodiment, aliphatic diisocyanates may be used wherein Y is an alkylene radical because these result in materials which exhibit improved stabilities towards UV radiation. The alkylenes comprising an α,ω-OH ending of (6) are, in at least one embodiment, polyalkylenes or polyoxyalkylenes. These are, for example, essentially devoid of contamination by monofunctional polyoxyalkylenes, trifunctional polyoxyalkylenes or polyoxyalkylenes of higher functionality. Use may be made here of polyether polyols, polytetramethylene diols, polyester polyols or polycaprolactone diols but also of polyalkylenes comprising an α,ω-OH ending based on poly(vinyl acetate), poly(vinyl acetate)/ethylene copolymers, poly(vinyl chloride) copolymers or polyisobutylene diols. In at least one embodiment, use is made of polyoxyalkylenes, and in a further embodiment, of polypropylene glycol. Such compounds are available commercially as base materials, inter alia, for polyurethane foams and for uses as coatings with molecular weights Mn of up to 10 000. Non-limiting examples include the Baycoll® polyether polyols and polyester polyols from Bayer AG, Germany, or the Acclaim® polyether polyols from Lyondell Inc., USA. Use may also be made of α,ω-alkylene diol monomers, such as ethylene glycol, propanediol, butanediol or hexanediol. Furthermore, the term "dihydroxylated compounds" as used herein, is also understood to mean bishydroxyalkylsilicones, such as those supplied, for example, by Goldschmidt under the names Tegomer H-Si 2111, 2311 and 2711.

The preparation of the copolymers described above of formula (I) can be carried out in solution but also in a solid form, continuously or batchwise.

If the amount of urethane or urea segments is large, a solvent having high solubility parameter, such as dimethylacetamide may be chosen. Use may also be made of THF. In at least one embodiment, the synthesis of the copolymer is carried out without solvent.

According to at least one embodiment of the present disclosure, synthesis is carried out in the absence of moisture and under a protective gas, for example, nitrogen or argon.

In at least one embodiment, the reaction is carried out in the presence of a catalyst. Examples of catalysts suitable for the preparation are dialkyltin compounds such as, for example, dibutyltin dilaurate and dibutyltin diacetate, and tertiary amines, such as N,N-dimethyl-cyclohexaneamine, 2-dimethylaminoethanol and 4-dimethylaminopyridine.

According to at least one embodiment of the present disclosure, the copolymer does not comprise polyurethane.

Also useful as a copolymer is dimethylpolysiloxane/urea, with the INCI name polyureadimethicone.

Such a polymer can be obtained, for instance, by a copolymerization of an α,ω-aminosilicone with a diisocyanate. Polymers corresponding to these characteristics are, for example, the products sold under the reference Wacker-Belsil® UD 60, Wacker-Belsil® UD 80, Wacker-Belsil® UD 140 and Wacker-Belsil® UD 200 by Wacker.

According to the present disclosure, the composition applied to the hair comprises at least one volatile nonsilicone organic solvent. As used herein, "volatile solvent" is understood to mean an organic compound which is liquid at ambient temperature (20° C.) and at atmospheric pressure and which exhibits a vapor pressure at 20° C. of greater than 0.1 mmHg, for example, a vapor pressure ranging from 0.1 and 300 mmHg, and further for example, a vapor pressure ranging from 0.5 and 200 mmHg.

Examples of volatile nonsilicone organic solvents include but are not limited to:

volatile $C_1$-$C_4$ alkanols, such as ethanol and isopropanol;

volatile $C_5$-$C_7$ alkanes, such as n-pentane, hexane, cyclopentane, 2,3-dimethylbutane, 2,2-dimethyl-butane, 2-methylpentane and 3-methylpentane;

esters of liquid $C_1$-$C_{20}$ acids and of volatile $C_1$-$C_8$ alcohols, such as methyl acetate, n-butyl acetate, ethyl acetate, propyl acetate, isopentyl acetate and ethyl 3-ethoxypropionate;

ketones which are volatile liquids at ambient temperature, such as methyl ethyl ketone, methyl isobutyl ketone, diisobutyl ketone, isophorone, cyclohexanone and acetone;

volatile polyols, such as propylene glycol;

volatile ethers, such as dimethoxymethane, diethoxyethane and diethyl ether;

volatile glycol ethers, such as 2-butoxyethanol, butyl diglycol, diethylene glycol monomethyl ether, propylene glycol n-butyl ether and propylene glycol monomethyl ether acetate;

volatile hydrocarbon oils, such as volatile hydrocarbon oils having from 8 to 16 carbon atoms and their mixtures, and, in at least one embodiment, branched $C_8$-$C_{16}$ alkanes, such as $C_8$-$C_{16}$ isoalkanes (also known as isoparaffins), isododecane, isodecane, and, for example, the oils sold under the Isopar or Permethyl trade names, and their mixtures. Non-limiting mention may also be made of isohexyl neopentanoates or isodecyl neopentanoate.

volatile $C_4$-$C_{10}$ perfluoroalkanes, such as dodecafluoropentane, tetradecafluorohexane and decafluoropentane;

volatile perfluorocycloalkanes, such as perfluoro-methylcyclopentane, 1,3-perfluorodimethylcyclo-hexane and perfluorodecalin, sold under the names of "Flutec PC1®", "Flutec PC3®" and "Flutec PC6®" by F2 Chemicals, and also perfluorodimethylcyclobutane and perfluoromorpholine;

volatile fluoroalkyl or heterofluoroalkyl compounds corresponding to the following formula:

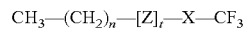

wherein t is 0 or 1;

n is chosen from 0, 1, 2 and 3;

X is chosen from a linear or branched divalent $C_2$-$C_5$ perfluoroalkyl radical;

Z is chosen from O, S and NR, wherein R is chosen from a hydrogen atom, a —$(CH_2)_n$—$CH_3$ and —$(CF_2)_m$—$CF_3$ radical and wherein m is chosen from 2, 3, 4 and 5.

A non-limiting example of a useful volatile fluoroalkyl or heterofluoroalkyl compound is methoxynonafluorobutane sold, for instance, under the name of "MSX 4518®" or "HFE-7100®" by 3M and the ethoxynona-fluorobutane sold, for example, under the name of "HFE-7200®" by 3M.

In at least one embodiment, the solvent is chosen so that its boiling point is less than 200° C.

In at least one other embodiment, the at least one volatile nonsilicone organic solvent is chosen from ethanol, isopropanol, acetone and isododecane.

As disclosed herein, the at least one volatile nonsilicone organic solvent is present in the composition in an amount ranging from 0.1% to 90% by weight, relative to the total weight of the composition, for example, ranging from 1% to 80% by weight and further for example, ranging from 5% to 70% by weight.

In at least one embodiment, the composition of the invention comprises at least one silicone compound exhibiting a viscosity of less than or equal to 100 centistokes (cSt), measured at 25° C. The at least one silicone compound of low viscosity can be chosen from linear and cyclic silicones having from 2 to 7 silicon atoms, and in at least one embodiment, may optionally comprise $C_1$-$C_{10}$ alkyl or alkoxy groups, for example octamethylcyclotetrasiloxane, decamethylcyclopentasiloxane, dodecamethylcyclohexasiloxane, heptamethylhexyltrisiloxane, heptamethylethyltrisiloxane, heptamethyloctyltrisiloxane, octamethyltrisiloxane, decamethyltetrasiloxane and mixtures thereof. According to at least one embodiment, the silicone compound is chosen from cyclopentadimethylsiloxane and dodecamethylcyclohexasiloxane.

In yet another embodiment, the silicone compound exhibits a viscosity of less than 50 centistokes.

Accordingly, the silicone compound with a viscosity of less than 100 cSt can be present in the composition, in at least one embodiment, in an amount ranging from 0.1% to 90% by weight, relative to the total weight of the composition, for example, ranging from 1% to 80% by weight and further for example, ranging from 5% to 70% by weight.

Other useful nonvolatile organic solvents include but are not limited to:
  nonvolatile aromatic alcohols, such as benzyl alcohol and phenoxyethanol;
  esters of liquid $C_1$-$C_{20}$ acids and of nonvolatile $C_1$-$C_8$ alcohols, such as isopropyl myristate;
  ethylene carbonate, propylene carbonate and butylene carbonate;
  nonvolatile polyols, such as glycerol, ethylene glycol, dipropylene glycol and butylene glycol;
  nonvolatile glycol ethers, such as diethylene glycol monoethyl ether and dipropylene glycol mono(n-butyl)ether;
  nonvolatile hydrocarbon oils, such as isohexadecane;
  nonvolatile liquid $C_{10}$-$C_{30}$ fatty alcohols, such as oleyl alcohol, liquid $C_{10}$-$C_{30}$ fatty alcohol esters, such as $C_{10}$-$C_{30}$ fatty alcohol benzoates, and mixtures thereof; polybutene oil, isononyl isononanoate, isostearyl malate, pentaerythrityl tetra-isostearate and tridecyl trimelate;
  nonvolatile perfluorinated solvents, such as perfluoroperhydrophenanthrene sold, for instance, under the name of "Flutec PC11®" by F2 Chemicals.

According to the present disclosure, the composition may also comprise at least one colored or coloring entity, for example, colored pigments, pearlescent agents, dye precursors and hydrophilic or hydrophobic direct dyes in order to obtain colored coatings.

In at least one embodiment, the composition may also comprise at least one filler. Fillers are generally compounds which are substantially colorless, solid at ambient temperature and atmospheric pressure and insoluble in the composition, even at temperatures greater than ambient temperature.

The fillers useful herein can be inorganic or organic. The fillers can be particles of any shape, such as platelet, spherical or oblong particles, whatever their crystallographic form (for example, sheet, cubic, hexagonal, orthorhombic). Moreover, these particles can be solid, hollow or porous and coated or uncoated.

Non-limiting examples of fillers which can be used in the compositions include inorganic fillers, such as talc, natural and synthetic mica, silica, kaolin, boron nitride, precipitated calcium carbonate, magnesium carbonate, basic magnesium carbonate and hydroxyapatite.

These inorganic fillers can be provided in the form of spherical particles with, for example, hollow silica microspheres, such as the "Silica Beads SB 700/HA®" or "Silica Beads SB 700®" from Maprecos or the "Sunspheres H-33®" and the "Sunspheres H-51®" from Asahi Glass.

It is beneficial for the inorganic particle to exhibit a number-average primary size ranging from 0.1 and 30 μm, for example, from 0.2 to 20 μm and further for example, from 0.5 to 15 μm. As used herein, "primary particle size" is understood to mean the maximum dimension possible to measure between two diametrically opposite points of an individual particle. The size of the organic particles can be determined by transmission electron microscopy or by measurement of the specific surface are via the BET method or via laser particle size determination.

In at least one embodiment of the present disclosure, the inorganic fillers are chosen from silica, talc and boron nitride.

In another embodiment, organic fillers may be useful in the context of the present disclosure. As used herein, "organic filler" is understood to mean a polymeric particle which can result from the polymerization of one or more monomers. The polymers constituting these organic particles may or may not be crosslinked. Examples of monomers that may be used, include, but are not limited to methacrylic and acrylic acid esters, such as methyl acrylates and methyl methacrylate, vinylidene chloride, acrylonitrile, styrene and derivatives thereof.

In at least one embodiment, the organic particles can exhibit a number-average primary size ranging from 1 μm to 30 μm, for example, from 1 μm to 20 μm and further for example, from 1 μm to 15 μm.

Useful organic particles that may be present in the cosmetic composition can be chosen, in a non-restrictive manner, from polyamide powders, acrylic polymer powders, for example, polymethyl methacrylate, acrylic copolymer powders, for instance, polymethyl methacrylate/ethylene glycol dimethylacrylate, polyallyl methacrylate/ethylene glycol dimethacrylate, ethylene glycol dimethacrylate/lauryl methacrylate copolymer or of polyacrylate/alkyl acrylate, polystyrene powders, polyethylene powders, for example, polyethylene/acrylic acid, and silicone resin microbeads.

Mention may be made, by way of representation and without applied limitation, as organic particles according to the present disclosure, of:
  polyamide (Nylon®) powders, for example those sold under the names "Orgasol® 4000" and "Orgasol® 2002 UD NAT COS 24" by Atochem,
  acrylic polymer powders, e.g., of polymethyl methacrylate, such as, for example, those sold under the name "Covabead® LH85" or "Covabead® PMMA" by Wacker or those sold under the name "Micropearl® MHB" by Matsumoto,
  acrylic copolymer powders, e.g., of polymethyl methacrylate/ethylene glycol dimethacrylate, such as those sold under the name of "Dow Corning 5640 Microsponge® Skin Oil Adsorber" by Dow Corning or those sold under the name "Ganzpearl® GMP-0820" by Ganz Chemical, of polyallyl methacrylate/ethylene glycol dimethacrylate, such as those sold under the name "Polypore® L200" or "Polypore® E200" by Amcol, of ethylene glycol dimethacrylate/lauryl methacrylate copolymer, such as those sold under the name "Polytrap® 6603" by Dow Corning, or of polyacrylate/ethylhexyl acrylate, such as those sold under the name "Techpolymer® ACX 806C" by Sekisui, polystyrene/divinylbenzene powders, such as those sold under the name "Techpolymer® SBX8" by Sekisui, polyethylene powders, such as of polyethylene/acrylic acid, sold under the name "Flobeads®" by Sumitomo, silicone resin microbeads, such as those sold under the names "Tospearl®" by Toshiba Silicone, in particular "Tospearl® 240A" and "Tospearl® 120A", acrylic polymer microspheres, such as those made of crosslinked acrylate copolymer, "Polytrap 6603 Adsorber®" from R P Scherrer, polyurethane powders, such as the hexamethylene diisocyanate and trimethylol hexyllactone copolymer powder sold under the name "Plastic Powder D-400®" by Toshiki, methyl acrylate or methacrylate polymer or copolymer microcapsules or also vinylidene chloride and acrylonitrile copolymer microcapsules, such as "Expancel®" from Expancel, crosslinked organopolysiloxane elastomer powders, such as those sold under the name "Trefil Powder E-506C" by Dow Corning, polyfluorinated powders, e.g., of polytetrafluoroethylene, for example that sold under the name "MP 400" by Dupont de Nemours.

In at least one embodiment, the organic particles used in the cosmetic composition in accordance with the present disclosure are chosen from polyamide powders and polymethyl methacrylate powders.

The colored or coloring entities and fillers can be present in the composition in an amount ranging from 0.001% to 20% by weight relative to the total weight of the composition, for instance, ranging from 0.1% to 10% by weight.

As disclosed herein, the cosmetic composition may comprise at least one polysiloxane in order to obtain better spreading and improved coating. The at least one polysiloxane may exhibit a viscosity greater than 100 cSt, for example, greater than 300 cSt. The viscosity of these polysiloxanes can be measured according to Standard ASTM D-445. Non-limiting examples of the at least one polysiloxane include silicone oils, gum and resins, grafted silicones and crosslinked silicones.

Non-limiting mention may be made of polysiloxanes with a viscosity of greater than 100 cSt, such as polydimethylsiloxanes, alkyl dimethicones, polyphenyl-methylsiloxanes, phenyl dimethicones, phenyl trimethicones and vinyl methyl methicones; and silicones modified by aliphatic and/or aromatic groups optionally fluorinated or by functional groups, such as hydroxyl, thiol and/or amine groups.

Suitable polysiloxanes may be chosen from the silicones of formula (I):

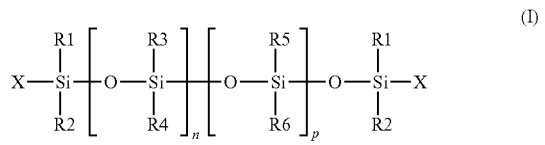

(I)

wherein:

R1, R2, R5 and R6, which may be identical or different, are chosen from a $C_1$-$C_6$ alkyl radical, R3 and R4, which may be identical or different, are chosen from a $C_1$-$C_6$ alkyl radical, a vinyl radical, an aryl radical, an amine radical and a hydroxyl radical and X is chosen from a $C_1$-$C_6$ alkyl radical, a hydroxyl radical, a vinyl radical and an amine radical, n and p are integers chosen so as to obtain a viscosity of greater than 300 cSt.

Non-limiting mention may be made of the following polydimethylsiloxanes:

the substituents R1 to R6 and X are methyl groups, such as that sold, for example, under the name Baysilicone TP 3898 by General Electric and that sold, for instance, under the name AK 500000 by Wacker, the substituents R1 to R6 and X are methyl groups, and p and n are such that the molecular weight is 120 000 g/mol, such as the product sold, for example, under the name Dow Corning 200 Fluid 60000 CS by Dow Corning, the substituents $R_1$ to $R_6$ and X are methyl groups and p and n are such that the molecular weight is 250 000 g/mol, such as the product sold, for instance, under the name Mirasil DM 500,000 by the company Rhodia and the product sold, for example, under the name Dow Corning 200 Fluid 500,000 cSt by Dow Corning, the substituents R1 to R6 are methyl groups, the X group is a hydroxyl group and n and p are such that the molecular weight of the polymer is 600 000 g/mol, such as the product sold, for instance, under the name SGM 36 by Dow Corning, dimethicones of the (polydimethylsiloxane) (methylvinylsiloxane) type, such as SE 63, sold by GE Bayer Silicones, poly(dimethylsiloxane)(diphenyl)(methylvinylsiloxane) copolymers and their mixtures.

In the case where the polysiloxane comprises a fluorinated group, the copolymers may exhibit the following structure:

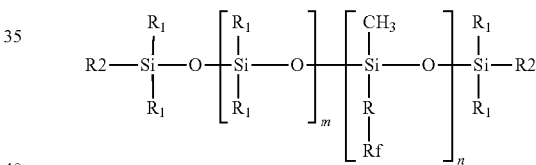

wherein:

R is chosen from a linear or branched divalent $C_1$-$C_6$ alkyl group, for example, a divalent methyl, ethyl, propyl or butyl group, Rf is a fluoroalkyl radical, for instance, a $C_1$-$C_{12}$ perfluoroalkyl radical, for example, a $C_1$-$C_9$ perfluoroalkyl radical. $R_1$ is chosen from, independently, a $C_1$-$C_{20}$ alkyl radical, a hydroxyl radical and a phenyl radical, $R_2$ is $R_1$ or Rf, m is chosen from 0 to 500, for example, from 0 to 200, and n is chosen from 1 to 1000, for instance, from 1 to 500.

In at least one embodiment, the $R_1$ groups are identical and are methyl radicals.

Non-limiting mention of polysiloxanes may be made in the present disclosure, for example, those sold by Shin-Etsu under the names 'FL-5', 'FL-10', 'X22-821' and 'X22-822' or 'FL-100', by Dow Corning under the name FS-1265 Fluid and by Phoenix Chemical under the Pecosil FS range under the names Pecosil FSL-150, Pecosil FSL-300, Pecosil FSH-150, Pecosil FSH-300, Pecosil FSU-150 and Pecosil FSU-300.

In at least one embodiment, the polysiloxanes may comprise a weight-average molecular weight that ranges from 1000 g/mol to 1 500 000 g/mol, for example, ranges from 20 000 g/mol to 1 000 000 g/mol.

In at least one embodiment of the present disclosure, the polysiloxane can be in the resin form. As used herein, "resin" is understood to mean a crosslinked or non-crosslinked three-dimensional structure. Non-limiting mention may be made of polysiloxane resins, for example, silsesquioxanes and siloxysilicates.

The nomenclature of silicone resins is known under the name of "MDTQ", the resin being described as a function of the various monomeric siloxane units which it comprises, each of the letters "MDTQ" characterizing a type of unit.

The letter M is the monofunctional-unit of formula $(CH_3)_3SiO_{1/2}$, wherein the silicon atom is connected to a single oxygen atom in the polymer comprising this unit.

The letter D is a difunctional unit $(CH_3)_2SiO_{2/2}$ wherein the silicon atom is connected to two oxygen atoms.

The letter T is a trifunctional unit of formula $(CH_3) SiO_{3/2}$.

In the M, D and T units defined above, at least one of the methyl groups can be substituted by an R group different from the methyl group, such as a hydrocarbon radical, for example, a $C_2$-$C_{10}$ alkyl radical or a phenyl group or alternatively, a hydroxyl group.

The letter Q is a tetrafunctional unit $SiO_{4/2}$, wherein the silicon atom is bonded to four oxygen atoms themselves bonded to the remainder of the polymer.

Various resins with different properties can be obtained from these different units. Examples of the properties of these polymers that vary according to the type of monomers (or units), include type and number of substituted radicals, the length of the polymer chain, the degree of branching and the size of the pendant chains.

Non-limiting mention may be made, for example, of the following silicone resins:

siloxysilicates, which can be trimethylsiloxysilicates of formula (XXI):

$$[(CH_3)_3-Si-O]_x-(SiO_{4/2})_y \quad (XXI)$$

(MQ units) wherein x and y are integers ranging from 50 to 80, polysilsesquioxanes of formula $(CH_3SiO_{3/2})_x$ (T units) wherein x is greater than 100 and at least one of the methyl radicals of which can be substituted by an R group as defined above, polymethylsilsesquioxanes, wherein none of the methyl radicals are substituted by another group. Such polymethylsilsesquioxanes are described, for example, in U.S. Pat. No. 5,246,694, the content of which is incorporated herein by reference.

Examples of commercially available polymethylsilsesquioxane resins that may be mentioned include, but are not limited to, those which are sold:

by Wacker under the reference Resin MK, such as Belsil PMS MK: polymer comprising $CH_3SiO_{3/2}$ repeat units (T units) which can also comprise up to 1% by weight of $(CH_3)SiO_{2/2}$ units (D units) and which exhibits an average molecular weight of approximately 10 000, by Shin-Etsu under the references KR-220L, which are composed of T units of formula $CH_3SiO_{3/2}$ and have Si—OH (silanol) end groups, under the reference KR-242A, which comprise 98% of T units and 2% of dimethyl D units and have Si—OH end groups, or under the reference KR-251, which combines 88% of T units and 12% of dimethyl D units and have Si—OH end groups.

Other useful resins are siloxysilicate resins, for example, trimethylsiloxysilicate (TMS) resins, optionally in the form of powders. Such resins are sold, for instance, under the reference SR1000 by General Electric or under the reference TMS 803 by Wacker. Non-limiting mention may also be made of the trimethylsiloxysilicate resins sold in a solvent, such as cyclomethicone, sold under the name "KR-7312J" by Shin-Etsu or "DC 749" or "DC 593" by Dow Corning.

According to at least one embodiment of the present disclosure, the polysiloxanes present in the composition are soluble or dispersible in the composition. In at least one embodiment, the silicone resin is solid at 25° C.

As disclosed herein, the composition can also comprise a grafted silicone polymer. As used herein, "grafted silicone polymer" is understood to mean a polymer comprising a polysiloxane portion and a portion composed of a nonsilicone organic chain, one of the two portions constituting the main chain of the polymer and the other being grafted to the said main chain.

Accordingly, the grafted silicone polymers that may be used in the cosmetic composition may include, but are not limited to polymers comprising a nonsilicone organic backbone grafted by monomers comprising a polysiloxane, polymers comprising a polysiloxane backbone grafted by nonsilicone organic monomers, and their mixtures.

In at least one embodiment, the nonsilicone organic monomers constituting the main chain of the grafted silicone polymer can be chosen from monomers comprising ethylenic unsaturation which can be polymerized by the radical route, monomers which can be polymerized by polycondensation, such as those forming polyamides, polyesters or polyurethanes, and ring-opening monomers, such as those of the oxazoline or caprolactone type.

Non-limiting mention may be made of the polymers comprising a nonsilicone organic backbone grafted by monomers comprising a polysiloxane in accordance with the present disclosure and can be chosen from those described in U.S. Pat. Nos. 4,693,935, 4,728,571 and 4,972,037 and European Patent Applications 0 412 704, 0 412 707, 0 640 105 and International Patent Application WO 95/00578. The copolymers described above are obtained by radical polymerization from monomers comprising ethylenic unsaturation and from silicone macromers having an end vinyl group or else copolymers obtained by reaction of a polyolefin comprising functionalized groups and of a polysiloxane macromer having an end functional group which reacts with the functionalized groups.

One exemplary family of grafted silicone polymers suitable for the implementation of the present disclosure is composed of grafted silicone copolymers comprising:

a) from 0.01 to 50% by weight of at least one polysiloxane macromer (C) of formula:

$$X(Y)_nSi(R)_{3-m}Z_m \quad (VI)$$

and b) from 0 to 98% by weight of at least one lipophilic monomer (A) of low lipophilic polarity comprising ethylenic unsaturation which can be polymerized by the radical route; and/or c) from 0 to 98% by weight of at least one polar hydrophilic monomer (B) comprising ethylenic unsaturation which can copolymerized with the monomer or monomers of the type (A);

wherein:

X is a vinyl group which can copolymerize with the monomers (A) and (B);

Y is a divalent bonding group;

R is chosen from a hydrogen atom, a $C_1$-$C_6$ alkyl, an alkoxy and a $C_6$-$C_{12}$ aryl;

Z is a monovalent polysiloxane unit having a number-average molecular weight of at least 500;

n is 0 or 1 and m is an integer ranging from 1 to 3, wherein the percentages are calculated with respect to the total weight of the monomers (A), (B) and (C).

According to at least one embodiment, such polymers have a number-average molecular weight ranging from 10 000 to 2 000 000 and a glass transition temperature Tg or a crystalline melting point Am of at least −20° C.

Non-limiting mention may be made, as examples of lipophilic monomers (A) of acrylic or methacrylic acid esters of $C_1$-$C_{24}$ alcohols; styrene; polystyrene macromers; vinyl acetate; vinyl propionate; α-methylstyrene; tert-butylstyrene; butadiene; cyclohexadiene; ethylene; propylene; vinyltoluene; esters of acrylic or methacrylic acid and of 1,1-dihydroperfluoroalkanols or of their homologs; esters of acrylic or methacrylic acid and of ω-hydridofluoroalkanols; esters of acrylic or methacrylic acid and of fluoroalkylsulphonamido alcohols; esters of acrylic or methacrylic acid and of fluoroalkyl alcohols; esters of acrylic or methacrylic acid and of alcohol fluoroethers; and their mixtures. In at least one embodiment, monomers (A) are chosen from the n-butyl methacrylate, isobutyl methacrylate, stearyl methacrylate, tert-butyl acrylate, tert-butyl methacrylate, 2-ethylhexyl methacrylate, methyl methacrylate, 2-(N-methyl-perfluorooctanesulphonamido)ethyl acrylate; 2-(N-butylperfluorooctanesulfonamido)ethyl acrylate, heptadecafluorooctylmethylaminoethyl methacrylate and their mixtures.

Mention may be made, as non-limiting examples of polar monomers (B), of acrylic acid, methacrylic acid, N,N-dimethylacrylamide, dimethylaminoethyl methacrylate, quaternized dimethylaminoethyl methacrylate, (meth)acrylamide, N-(t-butyl)acrylamide, maleic acid, maleic anhydride and their hemiesters, hydroxyalkyl(meth)acrylates, diallyldimethylammonium chloride, vinylpyrrolidone, vinyl ethers, maleimides, vinylpyridine, vinylimidazole, polar vinyl heterocyclic compounds, styrene sulphonate, allyl alcohol, vinyl alcohol, vinylcaprolactam or their mixtures. In at least one embodiment, the monomers (B) are chosen from acrylic acid, N,N-dimethylacrylamide, dimethylaminoethyl methacrylate, quaternized dimethylaminoethyl methacrylate, vinylpyrrolidone and their mixtures.

In at least one embodiment, the polysiloxane macromers (C) of formula (I) are chosen from those corresponding to the following formula (VII):

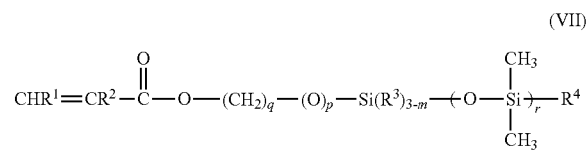

(VII)

wherein:
  $R^1$ is chosen from a hydrogen atom and a —COOH, for example, a hydrogen atom;
  $R^2$ is chosen from a hydrogen atom, methyl and a —CH$_2$COOH, for example, methyl;
  $R^3$ is chosen from $C_1$-$C_6$ alkyl, alkoxy, alkylamino, $C_6$-$C_{12}$ aryl and hydroxyl, for example, methyl;
  $R^4$ is chosen from $C_1$-$C_6$ alkyl, alkoxy, alkylamino, $C_6$-$C_{12}$ aryl and hydroxyl, for example, methyl;
  q is an integer ranging from 2 to 6, for example, 3;
  p is 0 or 1, for example, 0;
  r is an integer from 5 to 700;
  m is an integer ranging from 1 to 3, for example, 1.

According to at least one embodiment of the present disclosure, polysiloxane macromers may be used corresponding to the formula:

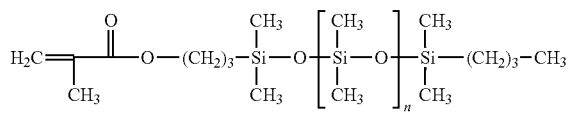

wherein n is a number ranging from 5 to 700.

In another embodiment, the copolymer may comprise a nonsilicone organic backbone grafted by monomers comprising a polysiloxane and can, for example, have the following structure:

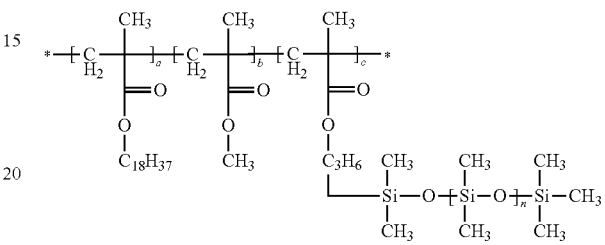

Such a polymer is sold, for example, under the name KP 561 by Shin-Etsu.

In yet another embodiment, the copolymer may comprise a nonsilicone organic backbone grafted by monomers comprising a polysiloxane and can for example, have the following structure:

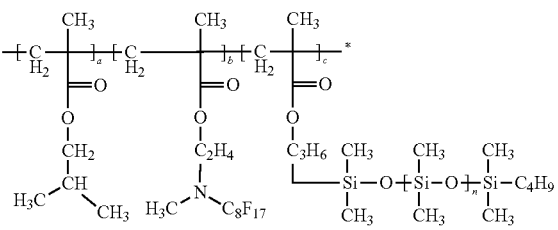

Such a polymer, Polysilicone 7, is sold, for instance, under the name SA70 by 3M.

Other useful copolymers comprising a nonsilicone organic backbone grafted by monomers comprising a polysiloxane that may be mentioned, include, but are not limited to KP545, KP574 and KP575, sold by Shin-Etsu.

Another embodiment of the present disclosure may comprise a copolymer capable of being obtained by radical polymerization from the mixture of monomers comprising:
  a) 60% by weight of tert-butyl acrylate;
  b) 20% by weight of acrylic acid;
  c) 20% by weight of silicone macromer of formula:

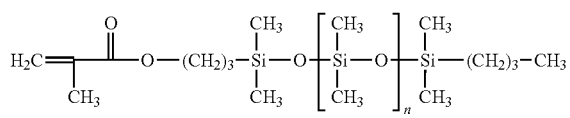

wherein n is a number ranging from 5 to 700; the percentages by weight being calculated with respect to the total weight of the monomers.

In yet another embodiment of the present disclosure the copolymer may be obtained by radical polymerization from the mixture of monomers comprising:

a) 80% by weight of tert-butyl acrylate;
b) 20% by weight of silicone macromer of formula:

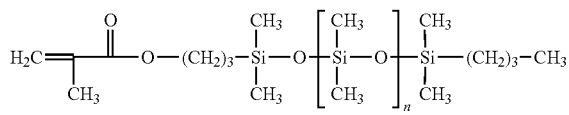

wherein n is a number ranging from 5 to 700; the percentages by weight being calculated with respect to the total weight of the monomers.

Another useful family of grafted silicone polymers comprising a nonsilicone organic backbone suitable for the implementation of the present disclosure are the grafted silicone copolymers capable of being obtained by reactive extrusion of a polysiloxane macromer having an end functional group which reacts with a polymer of the polyolefin type comprising reactive groups capable of reacting with the end functional group of the polysiloxane macromer in order to form a covalent bond which enables the silicone to be grafted to the main chain of the polyolefin. These polymers and their process for their preparation are described in International Patent Application WO 95/00578.

Examples of reactive polyolefins that may be used in the present disclosure may include, but are not limited to polyethylenes or polymers of monomers derived from ethylene, such as propylene, styrene, alkylstyrene, butylene, butadiene, (meth)acrylates, vinyl esters or equivalents, comprising reactive functional groups capable of reacting with the end functional group of the polysiloxane macromer. They are, for example, chosen from copolymers of ethylene or of ethylene derivatives and of monomers chosen from those comprising a carboxyl functional group, such as (meth)acrylic acid; those comprising an acid anhydride functional group, such as maleic anhydride; those comprising an acid chloride functional group, such as (meth)acryloyl chloride; those comprising an ester functional group, such as (meth)acrylates; and those comprising an isocyanate functional group.

In at least one embodiment, the silicone macromers are chosen from polysiloxanes comprising a functionalized group, at the end of the polysiloxane chain or close to the end of the said chain, from alcohols, thiols, epoxy compounds and primary and secondary amines and those corresponding to the following formula:

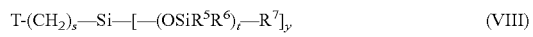

wherein:

T is chosen from $NH_2$, NHR', an epoxy functional group, OH and SH;

$R^5$, $R^6$, $R^7$ and R' are independently chosen from $C_1$-$C_6$ alkyl, phenyl, benzyl and $C_6$-$C_{12}$ alkylphenyl groups and from hydrogen;

s is a number from 2 to 100;

t is a number from 0 to 1000 and y is a number from 1 to 3.

The compounds of formula (VIII) have a number-average molecular weight ranging, in one embodiment, from 5000 to 300 000, such as from 8000 to 200 000, or further, from 9000 to 40 000.

As disclosed herein, the grafted silicone polymers may comprise a polysiloxane backbone grafted by nonsilicone organic monomers comprising a main silicone (or polysiloxane $\equiv$(Si—O—)$_n$) chain on which is grafted, within the said chain and optionally at least one of its ends, at least one organic group not comprising silicone. Accordingly, in at least one embodiment of the present disclosure, the silicone polymer comprising a polysiloxane backbone grafted by nonsilicone organic monomers employed comprises the result of the radical copolymerization between, on the one hand, at least one anionic nonsilicone organic monomer exhibiting an ethylenic unsaturation and/or one hydrophobic nonsilicone organic monomer exhibiting an ethylenic unsaturation and, on the other hand, a silicone exhibiting, in its chain, at least one functional group, and, in at least one embodiment, several functional groups, capable of reacting with the ethylenic unsaturations of the nonsilicone monomers with the formation of a covalent bond. In at least one embodiment, the functional groups are thio-functional groups.

According to at least one embodiment of the present disclosure, the anionic monomers possessing ethylenic unsaturation are chosen, alone or as a mixture, from unsaturated, linear or branched, carboxylic acids optionally partially or completely neutralized in the form of a salt, it being possible for this or these unsaturated carboxylic acids to be, in a further embodiment, chosen from acrylic acid, methacrylic acid, maleic acid, maleic anhydride, itaconic acid, fumaric acid and crotonic acid. Suitable salts are, for instance, the alkali metal, alkaline earth metal and ammonium salts. It should be noted that, likewise, in the final grafted silicone polymer, the organic group possessing an anionic nature which comprises the result of the radical (homo)polymerization of at least one anionic monomer of unsaturated carboxylic acid type can, after reaction, be postneutralized with a base (sodium hydroxide, ammonia, and the like) in order to convert it to the form of a salt In at least one embodiment of the present disclosure, the hydrophobic monomers comprising ethylenic unsaturation may be chosen, alone or as a mixture, from alkanol acrylic acid esters and/or alkanol methacrylic acid esters. The alkanols are, for example, $C_1$-$C_{18}$ and further for example, $C_1$-$C_{12}$ alkanols. In another embodiment, the monomers include, but are not limited to isooctyl(meth)acrylate, isononyl(meth)acrylate, 2-ethylhexyl(meth)acrylate, lauryl (meth)acrylate, isopentyl(meth)acrylate, n-butyl (meth)acrylate, isobutyl(meth)acrylate, methyl(meth)acrylate, tert-butyl (meth)acrylate, tridecyl(meth)acrylate, stearyl(meth)acrylate and mixtures thereof.

A family of silicone polymers comprising a polysiloxane backbone grafted by nonsilicone organic monomers which is useful herein comprises silicone polymers comprising, in their structure, units of following structure (IXb) and units of following structure (IX) and/or (IXa):

wherein:
the $G_1$ radicals, which may be identical or different, are chosen from a hydrogen atom, $C_1$-$C_{10}$ alkyl radicals and phenyl radicals;
the $G_2$ radicals, which may be identical or different, are $C_1$-$C_{10}$ alkylene groups;
$G_3$ is a polymer residue resulting from the (homo)polymerization of at least one anionic monomer comprising ethylenic unsaturation;
$G_4$ is a polymer residue resulting from the (homo)polymerization of at least one monomer of at least one hydrophobic monomer comprising ethylenic unsaturation;
m and n are 0 or 1;
a is an integer ranging from 0 to 50;
b is an integer ranging from 10 to 350; and
c is an integer ranging from 0 to 50;
with the proviso that one of a and c is other than 0.

In at least one embodiment of the present disclosure, the unit of formula (IX) above exhibits at least one of the following characteristics:
the $G_1$ radicals are independently alkyl radicals, and in one embodiment are methyl radicals;
n is not zero and the $G_2$ radicals are independently divalent $C_1$-$C_3$ radicals, and in one embodiment are propylene radicals;
$G_3$ is a polymer radical resulting from the (homo)polymerization of at least one ethylenic unsaturated monomer comprising a carboxylic acid, for example, acrylic acid and methacrylic acid;
$G_4$ is a polymer radical resulting from the homo (poly) merization of at least one monomer of the $C_1$-$C_{10}$ alkyl (meth)acrylate type, for instance, isobutyl and (meth) acrylate.

Non-limiting examples of silicone polymers corresponding to the formula (VI) are, for example, polydimethylsiloxanes (PDMSs) on which are grafted, via a connecting sequence of thiopropylene type, mixed polymer units of the poly(meth)acrylic acid type and of the poly(alkyl(meth)acrylate) type. Non-limiting mention may be made, of a compound corresponding to this definition, of polydimethyl/methylsiloxane comprising propyl thio-3 methyl acrylate/ methyl methacrylate/methacrylic acid groups or Polysilicone-8 sold under, for example, the name VS80 by 3M.

Suitable silicone polymers corresponding to the formula (VI) that may be used herein are polydimethylsiloxanes (PDMSs) on which are grafted, via a connecting sequence of thiopropylene type, polymer units of the poly(isobutyl(meth) acrylate) type.

In at least one embodiment, the number-average molecular weight of the silicone polymers comprising a polysiloxane backbone grafted by nonsilicone organic monomers varies from 10 000 to 1 000 000, for example, from 10 000 to 100 000.

Useful grafted silicone polymers are chosen from, but not limited to, alkyl methacrylate copolymers grafted by polydimethylsiloxane, copolymers of isobutyl methacrylate, copolymers of acrylic acid, copolymers of silicone macromer and polydimethyl/methylsiloxane comprising propyl thio-3 methyl acrylate/methyl methacrylate/methacrylic acid groups.

The composition of the present disclosure may also comprise a crosslinked silicone, such as a crosslinked organopolysiloxane elastomer, a silicone compound of high molecular weight exhibiting a three-dimensional structure, with the viscoelastic properties of a flexible solid material. This material is capable of returning to its original shape after it has been stretched. This elastomer is formed of polymer chains of high molecular weight, the mobility of which is limited by a uniform network of crosslinking points. These compounds have the property of absorbing certain solvents, such as silicone solvents, and thus of thickening them, while conferring, on the composition, very good cosmetic qualities, such as spreading qualities. These organopolysiloxanes can thus be provided in the dry powder form, in the form dispersed in an aqueous solution or in the form swollen in a solvent, the resultant product generally being a gel.

The synthesis of these organopolysiloxanes is described in the following patents:
U.S. Pat. No. 5,266,321 of Kobayashi Kose,
U.S. Pat. No. 4,742,142 of Toray Silicone,
U.S. Pat. No. 5,654,362 of Dow Corning Corp.,
French Patent Application 2 864 784.

The organopolysiloxane elastomers used in the composition in accordance with the present disclosure may be partially or completely crosslinked. They are generally provided in the form of particles, for example, the particles of an organopolysiloxane elastomer that has a number-average size ranging from 0.1 to 500 µm, for example, from 3 to 200 µm and further, for example from 3 to 50 µm. These particles can have any shape, for example, spherical, flat or amorphous.

The crosslinked organopolysiloxane elastomer may be obtained by a crosslinking addition reaction of a diorganopolysiloxane comprising at least one hydrogen atom bonded to a silicon atom and a diorganopolysiloxane having at least two groups comprising ethylenic unsaturation bonded to separate silicon atoms, for example, in the presence of a platinum catalyst; or by a crosslinking condensation/dehydrogenation reaction between a diorganopolysiloxane comprising hydroxyl endings and a diorganopolysiloxane comprising at least one hydrogen atom bonded to a silicon atom, for instance, in the presence of an organotin compound; or by a crosslinking condensation reaction of a diorganopolysiloxane comprising hydroxyl endings and of a hydrolysable organopolysilane; or by thermal crosslinking of an organopolysiloxane, for example, in the presence of an organoperoxide catalyst; or by crosslinking of an organopolysiloxane by high energy radiation, such as gamma rays, ultraviolet rays or an electron beam.

In at least one embodiment, the crosslinked organopolysiloxane elastomer is obtained by a crosslinking addition reaction of a diorganopolysiloxane (X) comprising at least one hydrogen atom bonded to a silicon atom and of a diorganopolysiloxane (XI) having at least two groups comprising ethylenic unsaturation each bonded to a separate silicon atom, for instance, in the presence of a platinum catalyst (XII), as, for example, described in European Patent Application 0 295 886.

The compound (X) is, in at least one embodiment, an organopolysiloxane comprising at least two hydrogen atoms bonded to separate silicon atoms in each molecule. The compound (X) can exhibit any molecular structure, for example, a linear chain or branched chain structure or a cyclic structure. The compound (X) can have a viscosity of 25° C. ranging from 1 to 50 000 centistokes in order to be highly miscible with the compound (XI).

In another embodiment, the organic groups bonded to the silicon atoms of the compound (X) can be alkyl groups, such as methyl, ethyl, propyl, butyl and octyl; substituted alkyl groups, such as 2-phenylethyl, 2-phenylpropyl and 3,3,3-trifluoropropyl; aryl groups, such as phenyl, tolyl and xylyl; substituted aryl groups, such as phenylethyl; and substituted monovalent hydrocarbon groups, such as an epoxy group, a carboxylate ester group and a mercapto group. The compound (X) can thus be chosen from methylhydropolysiloxanes comprising trimethylsiloxy endings, dimethylsiloxane/methylhydrosiloxane copolymers comprising trimethylsiloxy endings or dimethylsiloxane/methylhydrosiloxane cyclic copolymers.

In yet another embodiment, the compound (XI) is a diorganopolysiloxane having at least two lower alkenyl groups, for example $C_2$-$C_4$ alkenyl groups. Accordingly, the lower alkenyl group can be chosen from, but is not limited to vinyl, allyl and propenyl groups. These lower alkenyl groups can be situated in any position on the organopolysiloxane molecule and are, in at least one embodiment, situated at the ends of the organopolysiloxane molecule.

As used herein, the organopolysiloxane (XI) can have a branched-chain, linear-chain, cyclic or network structure, and in at least one embodiment, has a linear-chain structure. The compound (XI) can have a viscosity ranging from the liquid state to the gum state. In at least one embodiment, the compound (XI) has a viscosity of at least 100 centistokes at 25° C. In addition to the abovementioned alkenyl groups, the other organic groups bonded to the silicon atoms in the compound (XI) can be chosen, in a non-restrictive manner, from alkyl groups, such as methyl, ethyl, propyl, butyl or octyl; substituted alkyl groups, such as 2-phenylethyl, 2-phenylpropyl or 3,3,3-trifluoropropyl; aryl groups, such as phenyl, tolyl or xylyl; substituted aryl groups, such as phenylethyl; and substituted monovalent hydrocarbon groups, such as an epoxy group, a carboxylate ester group and a mercapto group.

Useful organopolysiloxanes (XI) that may be mentioned in the present disclosure may include, but are not limited to methylvinylpolysiloxanes, methylvinylsiloxane/dimethylsiloxane copolymers, dimethylpolysiloxanes comprising dimethylvinylsiloxy endings, dimethylsiloxane/methylphenylsiloxane copolymers comprising dimethylvinylsiloxy endings, dimethylsiloxane/diphenylsiloxane/methylvinylsiloxane copolymers comprising dimethylvinylsiloxy endings, dimethylsiloxane/methylvinylsiloxane copolymers comprising trimethylsiloxy endings, dimethylsiloxane/methylphenylsiloxane/methylvinylsiloxane copolymers comprising trimethylsiloxy endings, methyl(3,3,3-trifluoropropyl)polysiloxanes comprising dimethylvinylsiloxy endings and dimethylsiloxane/methyl(3,3,3-trifluoropropyl)siloxane copolymers comprising dimethylvinylsiloxy endings. In at least one embodiment, the organopolysiloxane elastomer can be obtained by reaction of a dimethylpolysiloxane comprising dimethylvinylsiloxy endings and of a methylhydropolysiloxane comprising trimethylsiloxy endings in the presence of a platinum catalyst.

In another embodiment, the sum of the number of ethylenic groups per molecule of the compound (XI) and of the number of hydrogen atoms bonded to silicon atoms per molecule of the compound (X) is at least 5.

In yet another embodiment, the compound (X) may be added in an amount such that the molecular ratio of the total amount of hydrogen atoms bonded to silicon atoms in the compound (X) to the total amount of all the groups comprising ethylenic unsaturation in the compound (XI) ranges from 1.5/1 to 20/1.

In another embodiment, the compound (XII) is the catalyst of the crosslinking reaction and may be chosen in a non-restrictive manner from chloroplatinic acid, chloroplatinic acid/olefin complexes, chloroplatinic acid/alkenylsiloxane complexes, chloroplatinic acid/diketone complexes, platinum black and platinum-on-support. The catalyst (XII) is added in a proportion of 0.1 to 1000 parts by weight, for example, of 1 to 100 parts by weight, as platinum metal proper per 1000 parts by weight of the total amount of the compounds (X) and (XI).

According to at least one embodiment, the crosslinked organopolysiloxane compound obtained can be a nonemulsifying or an emulsifying crosslinked organopolysiloxane compound. As used herein, "nonemulsifying" is understood to mean crosslinked organopolysiloxanes not comprising polyoxyalkylene units. As used herein, "emulsifying" is understood to mean crosslinked organopolysiloxane compounds having at least one polyoxyalkylene, for example, polyoxyethylene or polyoxypropylene, unit.

The crosslinked organopolysiloxane particles can be conveyed according to the present disclosure in a form of a gel composed of a crosslinked organopolysiloxane included in at least one hydrocarbon oil and/or one silicone oil. In these gels, the organopolysiloxane particles may be nonspherical particles. The crosslinked organopolysiloxane particles can also be provided in the form of a powder, for example, in the form of a spherical powder.

Non-limiting examples of nonemulsifying crosslinked organopolysiloxanes are described in U.S. Pat. Nos. 4,970,252, 4,987,169, 5,412,004, 5,654,362 and 5,760,116 and in Japanese Patent Application 61-194009.

Other useful non-emulsifying crosslinked organopolysiloxanes, according to the present disclosure may include, but are not limited to those sold, for example, under the names "KSG-6", "KSG-15", "KSG-16", "KSG-188", "KSG-31", "KSG-32", "KSG-33", "KSG-41", "KSG-42", "KSG-43", "KSG-44" and "USG-103" by Shin-Etsu, "DC 9040", "DC 9041", "DC 9509", "DC 9505", "DC 9506" and "DC 9045" by Dow Corning, "Gransil" by Grant Industries and "SFE 839" by General Electric.

In at least one embodiment, the emulsifying crosslinked organopolysiloxanes may comprise the polyoxyalkylene-modified organopolysiloxanes formed from divinyl compounds, for example, polysiloxanes comprising at least two vinyl groups, and reacting with Si—H bonds of a polysiloxane. Emulsifying crosslinked organopolysiloxanes are described for example, in U.S. Pat. Nos. 5,236,986, 5,412,004, 5,837,793 and 5,811,487.

Useful emulsifying crosslinked organopolysiloxanes according to the present disclosure may include those sold, for instance, under their names "KSG-21", "KSG-20", "KSG-30" and X-226146" by Shin-Etsu and "DC9010" and "DC9011" by Dow Corning.

In at least one embodiment, the crosslinked organopolysiloxane elastomer particles can be provided in the form of a crosslinked organopolysiloxane elastomer powder coated with silicone resin, for example, silsesquioxane resin, as described U.S. Pat. No. 5,538,793.

Such elastomers are sold, for instance, under the names "KSP-100", "KSP-101", "KSP-102", "KSP-103", "KSP-104" and "KSP-105" by Shin-Etsu.

Other useful crosslinked organopolysiloxane elastomers in the form of powders can be powders formed of hybrid silicone functionalized by fluoroalkyl groups, sold, for example, under the name "KSP-200" by Shin-Etsu; or powders formed of hybrid silicones functionalized by phenyl groups, sold, for instance, under the name "KSP-300" by Shin-Etsu.

Other useful crosslinked organopolysiloxanes, according to the present disclosure, can be provided in the form of dispersions of powders in water in the presence or absence of an emulsifying agent, such as, the compounds BY29-119, DC2-1997, EPSX001B, EPSX002B and EPSX004A from Dow Corning.

When at least one polysiloxane is present in the composition of the present disclosure, the at least one polysiloxane may have a viscosity of greater than 100 cSt and may be introduced in an amount ranging from 0.1% and 30% by weight, for example, ranging from 0.1%, and 20% by weight and further, for example, ranging from 0.1% and 10% by weight.

In at least one embodiment, the composition of the present disclosure can also comprise a nonsilicone polymer to improve either the intrinsic properties of the composition or the coating obtained during application to the individual hair or both.

Non-limiting examples of nonsilicone polymers may include, but are not limited to the following polymers:
  polymers soluble in a liquid organic medium, for example, fat-soluble polymers;
  polymers dispersible in an organic solvent medium, for instance, polymers in the form of nonaqueous dispersions of polymer particles with a primary size of less than 1 µm, that may be dispersions in silicone or hydrocarbon oils;
  polymers in the form of aqueous dispersions of polymer particles with a primary size of less than 1 µm, often known as "latexes" wherein the composition comprises an aqueous phase;
  water-soluble polymers wherein the composition comprises an aqueous phase or else the polymer is applied in pre- or post-treatment with regard to the PDMS/polyurea copolymer.

In at least one embodiment, the polymer which can be used in the composition can be anionic, cationic, nonionic or amphoteric.

Useful anionic polymers that may be present in the cosmetic composition include, but are not limited to carboxylic, sulfonic and phosphoric acid which have a number-average molecular weight ranging from 500 and 5 000 000.

In at least one embodiment, the carboxyl groups are contributed by unsaturated mono- or dicarboxylic acid monomers, such as those corresponding to the formula:

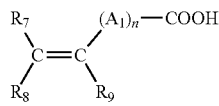

wherein
  n is an integer ranging from 0 to 10;
  A1 is a methylene group, optionally connected to the carbon atom of the unsaturated group or to the neighboring methylene group when n is greater than 1 via a heteroatom, such as oxygen or sulfur;
  $R_7$ is chosen from a hydrogen atom, a phenyl group and a benzyl group;
  $R_8$ is chosen from a hydrogen atom, a lower alkyl, and a carboxyl group; and
  $R_9$ is chosen from a hydrogen atom, a lower alkyl group, a —$CH_2$—COOH, a phenyl group and a benzyl group.

In the abovementioned formula, in at least one embodiment, a lower alkyl group is a $C_1$-$C_4$ group, for example, methyl and ethyl groups.

In another embodiment, the anionic polymers comprising carboxyl groups may include, but are not limited to:
A) Homo- or copolymers of acrylic and methacrylic acid and their salts, for example, the products sold under the names Versicol® E or K by Allied Colloid and Ultrahold® by BASF, the copolymers of acrylic acid and of acrylamide sold in the form of their sodium salts under the names Reten 421, 423 or 425 by Hercules or the sodium salts of polyhydroxycarboxylic acids.

B) Copolymers of acrylic and methacrylic acid with a monoethylenic monomer, such as ethylene, styrene, vinyl esters and esters of acrylic and methacrylic acid, optionally grafted onto a polyalkylene glycol, such as polyethylene glycol, and optionally crosslinked. Such polymers are described for example, in French Patent 1 222 944 and German Patent Application 2 330 956, wherein the copolymers of this type comprise, in their chain, an optionally N-alkylated and/or -hydroxyalkylated acrylamide unit, such as described in Luxembourgian Patent Applications 75370 and 75371 or provided under the name Quadramer by American Cyanamid. Non-limiting mention may also be made of copolymers of acrylic acid and of $C_1$-$C_4$ alkyl methacrylate and terpolymers of vinylpyrrolidone, of acrylic acid and of $C_1$-$C_{20}$ alkyl methacrylate, for example, lauryl methacrylate, such as that sold by ISP under the name Acrylidone® LM, and methacrylic acid/ethyl acrylate/tert-butyl acrylate terpolymers, such as the product sold, for example, under the name Luvimer® 100 P by BASF.

Non-limiting mention may also be made of the methacrylic acid/acrylic acid/ethyl acrylate/methyl methacrylate copolymers in aqueous dispersion sold, for example, under the name Amerhold® DR 25 by Amerchol.

C) Copolymers of crotonic acid, such as those comprising, in their chain, vinyl acetate or propionate units and optionally other monomers, such as allyl or methallyl esters, vinyl ether or vinyl ester of a linear or branched saturated carboxylic acid comprising a long hydrocarbon chain, such as those comprising at least 5 carbon atoms and optionally being possible for these polymers to be grafted or crosslinked, or alternatively another monomer which is a vinyl, allyl or methallyl ester of an α- or β-cyclic carboxylic acid. Such polymers are described, for example, in French Patents 1 222 944, 1 580 545, 2 265 782, 2 265 781, 1 564 110 and 2 439 798. Examples of commercial products include, but are not limited to the Resins 28-29-30, 26-13-14 and 28-13-10 sold by National Starch.

D) Copolymers of $C_4$-$C_8$ monounsaturated carboxylic acids or anhydrides chosen from:
  copolymers comprising (i) at least one maleic, fumaric or itaconic acid or anhydride and (ii) at least one monomer chosen from vinyl esters, vinyl ethers, vinyl halides, phenylvinyl derivatives, and acrylic acid and its esters thereof, the anhydride functional groups of these copolymers optionally being monoesterified or monoamidated. Such polymers are described, for example, in U.S. Pat. Nos. 2,047,398, 2,723, 248 and 2,102,113 and British Patent 839 805. Examples of commercial products include, but are not limited to those sold under the names Gantrez® AN or ES by ISP;
  copolymers comprising (i) at least one maleic, citraconic or itaconic anhydride unit and (ii) at least one monomer chosen from allyl and methallyl esters, optionally comprising at least one of the following: acrylamide, methacrylamide, α-olefin, acrylic and methacrylic ester, acrylic and methacrylic acid, and vinylpyrrolidone groups in their chain, the anhydride functional groups of these copolymers optionally being monoesterified or monoamidated.

These polymers are, for example, described in French Patents 2 350 384 and 2 357 241.

E) Polyacrylamides comprising carboxylate groups.

The homopolymers and copolymers comprising sulfo groups are polymers comprising vinylsulfonic, styrenesulfonic, naphthalenesulfonic or acrylamidoalkylsulfonic units.

These polymers can, for example, be chosen from:

salts of polyvinylsulfonic acid that have a molecular weight ranging from 1000 to 100 000, and copolymers with an unsaturated comonomer, such as acrylic or methacrylic acids and their esters thereof, as well as acrylamide or its derivatives, vinyl ethers and vinylpyrrolidone;

salts of polystyrenesulfonic acid, such as the sodium salts sold, for example, under the names Flexan® 500 and Flexan® 130 by National Starch. These compounds are also described in French Patent 2 198 719;

salts of polyacrylamidosulfonic acids, such as those mentioned in U.S. Pat. No. 4,128,631 and the polyacrylamidoethylpropanesulfonic acid sold, for instance, under the name Cosmedia Polymer HSP 1180 by Henkel;

sulfonic polyesters. As used herein, "sulfonic polyesters" is understood to mean copolyesters obtained by polycondensation of at least one dicarboxylic acid or of one of its esters, of at least one diol and of at least one sulfoaryldicarboxyl difunctional compound substituted on the aromatic nucleus by an —$SO_3M$ group wherein M is chosen from a hydrogen atom and a metal ion, such as $Na^+$, $Li^+$ and $K^+$.

Water-dispersible sulfonic polyesters generally exhibit a weight-average molecular weight ranging from 1000 to 60 000, for example, from 4000 to 20 000, as determined by gel permeation chromatography (or GPC).

The glass transition temperature of these sulfonic polyesters may range from 10° C. to 100° C., for example, from 25° C. to 60° C.

Homopolymers and copolymers comprising sulfo groups are described in more detail in U.S. Pat. Nos. 3,734,874, 3,779,993, 4,119,680, 4,300,580, 4,973,656, 5,660,816, 5,662,893 and 5,674,479.

In at least one embodiment of the present disclosure, the sulfonic polyesters may comprise at least one unit derived from isophthalic acid, from salt of sulfoaryldicarboxylic acid and from diethylene glycol and furthermore, the sulfonic polyesters that may be used in the present disclosure may be obtained from isophthalic acid, from sodium salt of sulfoisophthalic acid, from diethylene glycol and from 1,4-cyclohexanedimethanol.

Examples of sulfonic polyesters that may be mentioned include, but are not limited to those known under the INCI name Diglycol/CHDM/Isophthalates/SIP and sold, for example, under the trade name Eastman AQ® by Eastman Chemical and further for example, those sold, for instance, under the trade name Eastman AQ 48®.

Other useful anionic polymers according to the present disclosure, include, but are not limited to the anionic branched block polymer sold, for example, under the name Fixate G-100 by Noveon.

Anionic polyurethanes may also be used as polymers according to at least one embodiment which may or may not be functionalized and which may or may not be silicone-comprising.

Examples of polyurethanes include, but are not limited to those described in European Patent Applications 0 656 021, 0 751 162, 0 637 600, 0 648 485 and 0 619 111 and French Patent 2 743 297, and in International Application WO 94/03510 of BASF.

Non-limiting mention may be made of polyurethanes which are products sold, for example, under the names Luviset PUR® and Luviset® Si PUR by BASF.

Other useful anionic polymers within the context of the present disclosure may include, but are not limited to branched block copolymers comprising, as main monomers, at least one $C_{1-20}$ alkyl acrylate and/or at least one N-mono- or N,N-di($C_{2-12}$ alkyl)(meth)acrylamide, and acrylic acid and/or methacrylic acid.

These branched sequential (or block) copolymers exhibit a structure composed of hydrophobic blocks attached to a certain number of hydrophilic blocks via bifunctional units which may also exhibit at least two glass transition temperatures.

In at least one embodiment, these copolymers may exhibit the following composition:

from 26 mol % to 36 mol % of acrylic acid
from 27.5 mol % to 30.5 mol % of n-butyl acrylate
from 33.3 mol % to 45.3 mol % of methacrylic acid
from 0.48 mol % to 0.92 mol % of allyl methacrylate As used herein, the most hydrophobic blocks have a molecular weight ranging from 10 000 to 100 000 daltons and the most hydrophilic blocks have a molecular weight ranging from 1000 to 100 000 daltons.

The above polymers are in the anionic form, such that they are converted to salts by partial or complete neutralization of the (meth)acrylic acid groups. In at least one embodiment, non-limiting mention may be made of neutralizing agents, such as 2-amino-2-methyl-1-propanol and sodium hydroxide.

Such polymers are described, for example, in International Patent Application WO 00/40628 and are sold, for example, under the names EX-SDR-26® and EX-SDR-450 by Goodrich.

Examples of useful anionic polymers include, but are not limited to are acrylic acid copolymers, such as the acrylic acid/ethyl acrylate/N-tert-butylacrylamide terpolymers sold, for instance, under the name Ultrahold® Strong by BASF, copolymers derived from crotonic acid, such as the vinyl acetate/vinyl tert-butylbenzoate/crotonic acid terpolymers and the crotonic acid/vinyl acetate/vinyl neododecanoate terpolymers sold, for example, under the name Resin 28-29-30 by National Starch, polymers derived from maleic, fumaric or itaconic acids or anhydrides with vinyl esters, vinyl ethers, vinyl halides, phenylvinyl derivatives, or acrylic acid and its esters, such as the monoesterified methyl vinyl ether/maleic anhydride copolymers sold, for example, under the name Gantrez® by ISP, the copolymers of methacrylic acid and of methyl methacrylate sold, for instance, under the name Eudragit® L by Rohm Pharma, the copolymers of methacrylic acid and of ethyl acrylate sold, for example, under the name Luvimer® MAEX or MAE by BASF, the vinyl acetate/crotonic acid copolymers sold for example, under the name Luviset CA 66 by BASF and the vinyl acetate/crotonic acid copolymers grafted by polyethylene glycol sold, for instance, under the name Aristoflex® A by BASF, and the polymer sold, for example, under the name Fixate G-100 by Noveon.

In at least one further embodiment, the anionic polymers may be chosen from the monoesterified methyl vinyl ether/maleic anhydride copolymers sold, for example, under the name Gantrez® ES 425 by ISP, the acrylic acid/ethyl acrylate/N-tert-butylacrylamide terpolymers sold, for instance, under the name Ultrahold® Strong by BASF, the copolymers of methacrylic acid and of methyl methacrylate sold, for example, under the name Eudragit® L by Rohm Pharma, the vinyl acetate/vinyl tert-butyl-benzoate/crotonic acid terpolymers and the crotonic acid/vinyl acetate/vinyl neododecanoate terpolymers sold, for instance, under the name Resin 28-29-30 by National Starch, the copolymers of methacrylic acid and of ethyl acrylate sold, for example, under the name Luvimer® MAEX or MAE by BASF, the vinylpyrrolidone/acrylic acid/lauryl methacrylate terpolymers sold, for instance, under the name Acrylidone® LM by ISP or the polymer sold, for example, under the name Fixate G-100 by Noveon.

In at least one embodiment, non-limiting mention may be made of cationic polymers, which are understood to mean polymers comprising cationic groups or groups which can be ionized to give cationic groups.

In at least one embodiment, cationic polymers are chosen from those which comprise primary, secondary, tertiary and/or quaternary amine groups which can either form part of the polymer chain or be carried by a side substituent.

In another embodiment, the cationic polymers that may be used, may have a molecular weight ranging from 1000 to $15 \times 10^6$.

In yet another embodiment, the cationic polymers that may be used are those which may comprise at least 10% by weight of amine groups or quaternary ammonium groups, the degree of quaternization of which, expressed as cationic equivalent per gram of polymer, is, for example, at least 0.05 cationic meq./g (meq.: milliequivalent).

According to at least one embodiment, when the cationic polymer carries amine or quaternary ammonium groups by a side substituent, the polymer chain is for example, an acrylic, vinyl or peptide chain.

Further non-limiting mention may more be made, among cationic polymers, of quaternized proteins and polymers of the polyamine, polyaminoamide and poly(quaternary ammonium) type.

The polymers can be linear, branched, possess a block structure, a comb structure or a dendritic structure and/or be in the form of a latex in water or in a concentrated saline solution.

Non-limiting mention may be made, by way of example, of quaternized proteins, such as chemically modified polypeptides carrying quaternary ammonium groups at the chain end or grafted to the chain. Non-limiting mention may be made, among these proteins, of:

a) collagen hydrolysates carrying triethylammonium groups, such as the products sold under the name "Quat-Pro E" by Maybrook and called, in the CTFA dictionary, "Triethonium Hydrolysed Collagen. Ethosulphate";

b) collagen hydrolysates carrying trimethylammonium or trimethylstearylammonium chloride groups, sold under the name of Quat-Pro S by Maybrook and called, in the CTFA dictionary, "Steartrimonium Hydrolysed Collagen";

c) protein hydrolysates carrying, on the polypeptide chain, quaternary ammonium groups comprising at least one alkyl radical having from 1 to 18 carbon atoms.

Non-limiting mention may be made, among these protein hydrolysates, inter alia, of those sold by Croda: Croquat L, Croquat M, Croquat S or Crotein Q; or the products sold by Inolex under the name "Lexein QX 3000", called, in the CTFA dictionary, "Cocotrimonium Collagen Hydrolysate".

Non-limiting mention may also be made, among quaternized proteins, of quaternized plant proteins, such as wheat, maize or soya proteins; mention may be made, as quaternized wheat proteins, of those sold by Croda under the names "Hydrotriticum WQ or QM", called, in the CTFA dictionary, "Cocodimonium Hydrolysed Wheat Protein", "Hydrotriticum QL", called, in the CTFA dictionary, "Laurdimonium Hydrolysed Wheat Protein", or "Hydrotriticum QS", called, in the CTFA dictionary, "Steardimonium Hydrolysed Wheat Protein".

Also useful as cationic polymers that may be present in the composition are the cationic polysaccharides. Examples of cationic polysaccharides may include, but are not limited to polysaccharides comprising quaternary ammonium, such as those described in U.S. Pat. Nos. 3,589,578 and 4 031 307, and guar gums comprising trialkyl-ammonium cationic groups. Such products are sold, for example, under the trade names of Jaguar C13S, Jaguar C 15 and Jaguar C 17 by Meyhall.

Non-limiting mention may also be made of quaternary copolymers of vinylpyrrolidone and of vinylimidazole; cationic cellulose derivatives, such as copolymers of cellulose or of cellulose derivatives grafted with a water-soluble monomer comprising a quaternary ammonium and described, for example, in U.S. Pat. No. 4,131,576, such as hydroxyalkylcelluloses, such as hydroxymethyl-, hydroxyethyl- or hydroxypropylcelluloses, grafted, for instance, with a methacryloyloxyethyltrimethylammonium, methacrylamidopropyltrimethylammonium or dimethyldiallylammonium salt.

The products sold corresponding to this definition are, for example, the products sold under the name "Celquat L 200" and "Celquat H 100" by National Starch.

Other non-limiting examples of cationic polymers are, for example, polymers of the polyamine, polyaminoamide or poly(quaternary ammonium) type.

These polymers which can be used in accordance with the present disclosure are chosen, for example, from:

(1) Homopolymers or copolymers derived from acrylic or methacrylic esters or amides comprising at least one of the units of the following formulae:

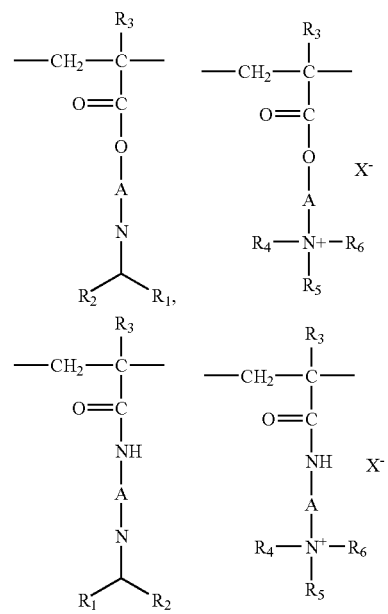

wherein:

$R_3$, which may be identical or different, is chosen from a hydrogen atom and a $CH_3$ radical;

A, which may be identical or different, is chosen from a linear or branched $C_1$-$C_6$ alkyl group, for example, ethyl or propyl, and a $C_1$-$C_4$ hydroxyalkyl group;

$R_4$, $R_5$ and $R_6$, which may be identical or different, are chosen from a $C_1$-$C_{18}$ alkyl-group and a benzyl radical, for example, a $C_1$-$C_6$ alkyl group;

$R_1$ and $R_2$, which may be identical or different, are chosen from a hydrogen atom, and a $C_1$-$C_6$ alkyl group, for example, methyl and ethyl;

X is an anion derived from an inorganic or organic acid, such as a methosulphate anion or a halide, such as chloride or bromide.

In at least one embodiment, the copolymers of family (1) can additionally comprise one or more units deriving from monomers which can be chosen from acrylamides, methacrylamides, diacetone acrylamides, acrylamides and methacrylamides substituted on the nitrogen by lower ($C_1$-$C_4$) alkyls, acrylic or methacrylic acids or their esters, vinyllactams, such as vinylpyrrolidone or vinylcaprolactam, or vinyl esters.

Non-limiting mention may be made, among these copolymers of family (1), of:

copolymers of acrylamide and of dimethylaminoethyl methacrylate quaternized with dimethyl sulfate or with a methyl halide, such as that sold under the name Hercofloc by Hercules, copolymers of acrylamide and of methacryloyloxyethyltrimethylammonium chloride, described, for example, in European Patent Application 080 976 and sold under the name Bina Quat P 100 by Ciba-Geigy, the copolymers of acrylamide and of methacryloyloxyethyltrimethylammonium methosulphate sold, for instance, under the name Reten by Hercules, vinylpyrrolidone/dialkylaminoalkyl acrylate or methacrylate copolymers, which may or may not be quaternized. These polymers are described in detail in French Patents 2 077 143 and 2 393 573 and are sold, for example, under the name "Gafquat" by GAF Corporation, such as "Gafquat 734 or 755", or else the product known as "Copolymer 937", polymers comprising a fatty chain and comprising a vinylpyrrolidone unit, such as the products sold under the names Styleze W20 and Styleze W10 by ISP, dimethylaminoethyl methacrylate/vinylcaprolactam/vinylpyrrolidone terpolymers, such as the product sold under the name Gaffix VC 713 by ISP, and vinylpyrrolidone/quaternized-dimethylaminopropylmethacrylamide copolymers, such as the products sold under the name "Gafquat® HS 100" by ISP.

(2) Polymers composed of piperazinyl units and of divalent, straight- or branched-chain alkylene or hydroxyalkylene radicals, optionally interrupted by oxygen, sulfur or nitrogen atoms or by aromatic or heterocyclic rings, as well as the oxidation and/or quaternization products of these polymers. Such polymers are described, for instance, in French Patents 2 162 025 and 2 280 361.

(3) Water-soluble polyaminoamides prepared, in at least one embodiment, by polycondensation of an acidic compound with a polyamine; these polyaminoamides can be crosslinked by an epihalohydrin, a diepoxide, a dianhydride, an unsaturated dianhydride, a bisunsaturated derivative, a bishalohydrin, a bisazetidinium, a bishaloacyldiamine or an alkyl bishalide or alternatively by an oligomer resulting from the reaction of a bifunctional compound reactive with respect to a bishalohydrin, a bisazetidinium, a bishaloacyldiamine, an alkyl bishalide, an epihalohydrin, a diepoxide or a bisunsaturated derivative; the crosslinking agent being used in proportions ranging from 0.025 to 0.35 mol per amine group of the polyaminoamide; these polyaminoamides can be alkylated or, if they comprise one or more tertiary amine functional groups, quaternized. Such polymers are described in French Patents 2 252 840 and 2 368 508.

(4) Polyaminoamide derivatives resulting from the condensation of polyalkylenepolyamines with polycarboxylic acids, followed by an alkylation by bifunctional agents. Non-limiting mention may be made, for example, of adipic acid/dialkylaminohydroxyalkyldialkylenetriamine polymers wherein the alkyl radical comprises from 1 to 4 carbon atoms, for example, methyl, ethyl or propyl. Such polymers are described in French Patent 1 583 363.

Non-limiting mention may also be made of the adipic acid/dimethylamino-hydroxypropyl/diethylenetriamine polymers sold, for example, under the name "Cartaretin F, F4 or F8" by Sandoz.

(5) Polymers obtained by reaction of a polyalkylenepolyamine comprising two primary amine groups and at least one secondary amine group with a dicarboxylic acid chosen from diglycolic acid and saturated aliphatic dicarboxylic acids comprising from 3 to 8 carbon atoms. In at least one embodiment, the molar ratio of polyalkylenepolyamine to dicarboxylic acid may range from 0.8:1 to 1.4:1. The polyaminoamide resulting there from may react with epichlorohydrin in a molar ratio of epichlorohydrin in relation to the secondary amine group of the polyaminoamide in a range from 0.5:1 to 1.8:1. Such polymers are described, for example, in U.S. Pat. Nos. 3,227,615 and 2 961 347.

Polymers of this type are, for example, sold under the name "Hercosett 57" by Hercules Inc. in the case of the adipic acid/epoxypropyl/diethylenetriamine copolymer.

(6) Cyclopolymers of alkyldiallylamine or of dialkyldiallylammonium, such as the homopolymers or copolymers comprising, as main constituent of the chain, units corresponding to the formulae (I) or (I'):

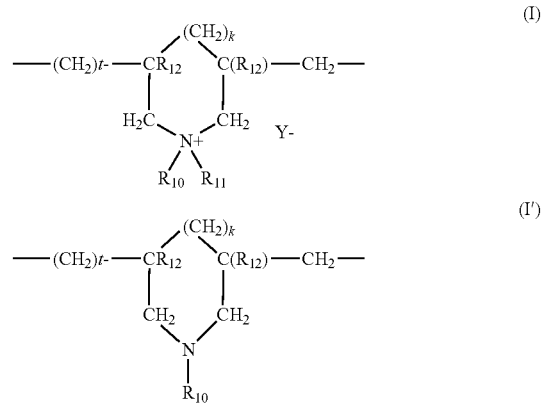

wherein:
k and t are equal to 0 or 1;
the sum k+t is 1;
$R_{12}$ is chosen from a hydrogen atom and a methyl radical;
$R_{10}$ and $R_{11}$, independently of one another, are chosen from a $C_1$-$C_6$ alkyl group, a hydroxyalkyl group in which the alkyl group has, in at least one embodiment, 1 to 5 carbon atoms, and a lower ($C_1$-$C_4$) amidoalkyl group or alternatively, $R_{10}$ and $R_{11}$ may form, together with the nitrogen atom to which they are attached, heterocyclic groups, such as piperidinyl or morpholinyl;

$Y^-$ is an anion, such as bromide, chloride, acetate, borate, citrate, tartrate, bisulphate, bisulphite, sulphate and phosphate. These polymers are described, for example, in French Patent 2 080 759 and in its Certificate of Addition 2 190 406.

In at least one embodiment, $R_{10}$ and $R_{11}$, independently of one another, are $C_1$-$C_4$ alkyl groups.

Non-limiting mention may be made, among the polymers defined above, of the homopolymer of dimethyldiallylammonium chloride sold, for example, under the name "Merquat 100" by Nalco (and its homologues of low weight-average molar masses) and of the copolymers of diallyldimethylammonium chloride and of acrylamide.

(7) The quaternary diammonium polymers comprising repeating units corresponding to the formula (II):

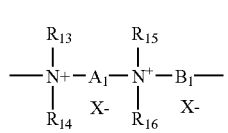

(II)

wherein:

$R_{13}$, $R_{14}$, $R_{15}$ and $R_{16}$, which may be identical or different, are chosen from an aliphatic, alicyclic and arylaliphatic radicals comprising from 1 to 20 carbon atoms and lower aliphatic hydroxyalkyl radicals or alternatively, $R_{13}$, $R_{14}$, $R_{15}$ and $R_{16}$, together or separately, form, with the nitrogen atoms to which they are attached, heterocycles optionally comprising a second heteroatom other than nitrogen or else $R_{13}$, $R_{14}$, $R_{15}$ and $R_{16}$ may be chosen from a linear or branched $C_1$-$C_6$ alkyl radical substituted by a nitrile, ester, acyl, amide and —CO—O—$R_{17}$-D or —CO—NH—$R_{17}$-D group, wherein $R_{17}$ is an alkylene and D a quaternary ammonium group;

$A_1$ and $B_1$ are chosen from polymethylene groups comprising from 2 to 20 carbon atoms which can be linear or branched and saturated or unsaturated, and which can comprise, bonded to or inserted into the main chain, one or more aromatic rings or one or more oxygen or sulfur atoms or sulfoxide, sulfone, disulfide, amino, alkylamino, hydroxyl, quaternary ammonium, ureido, amide or ester groups, and $X^-$ is an anion derived from an inorganic or organic acid;

$A_1$, $R_{13}$ and $R_{15}$ can form, with the two nitrogen atoms to which they are attached, a piperazine ring; in addition, if $A_1$ is a linear or branched and saturated or unsaturated alkylene or hydroxyalkylene radical, $B_1$ may be a —$(CH_2)_n$—CO-D-OC—$(CH_2)_n$— group wherein D is:

a) a glycol residue of formula: —O—Z—O—, wherein Z is a linear or branched hydrocarbon radical or a group corresponding to one of the following formulae:

—($CH_2$—$CH_2$—O)$_x$—$CH_2$—$CH_2$—

—[$CH_2$—CH($CH_3$)—O]$_y$—$CH_2$—CH($CH_3$)— wherein x and y are integers ranging from 1 to 4, representing a defined and unique degree of polymerization, or any number from 1 to 4, representing a mean degree of polymerization;

b) a bissecondary diamine residue, such as a piperazine derivative;

c) a bisprimary diamine residue of formula: —NH—Y—NH—, wherein Y is a linear or branched hydrocarbon radical or else the divalent radical

—$CH_2$—$CH_2$—S—S—$CH_2$—$CH_2$—;

d) a ureylene group of formula: —NH—CO—NH—.

In at least one embodiment, $X^-$ is an anion, such as chloride or bromide.

The above-mentioned polymers have, in at least one embodiment, a number-average molar mass ranging from 1000 to 100 000.

Such polymers of this type are described, for example, in French Patents 2 320 330, 2 270 846, 2 316 271, 2 336 434 and 2 413 907 and U.S. Pat. Nos. 2,273,780, 2,375,853, 2,388, 614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

Other useful polymers according to the present disclosure may include those composed of repeating units corresponding to the formula (a):

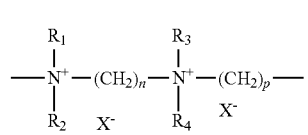

(a)

wherein:

$R_1$, $R_2$, $R_3$ and $R_4$, which may be identical or different, are chosen from $C_1$-$C_4$ alkyl and hydroxy($C_1$-$C_4$)alkyl radicals;

n and p are integers ranging from 2 to 20; and $X^-$ is an anion derived from an inorganic or organic acid.

In at least one embodiment, $R_1$, $R_2$, $R_3$ and $R_4$ are methyl radicals and n=3, p=6 and X=Cl; this product is known as Hexadimethrine chloride according to the INCI (CTFA) nomenclature.

(8) Poly(quaternary ammonium) polymers comprising units of formula (III):

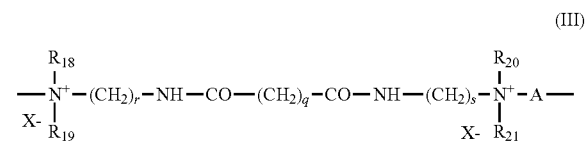

(III)

wherein:

$R_{18}$, $R_{19}$, $R_{20}$ and $R_{21}$, which may be identical or different, are chosen from hydrogen atom and methyl, ethyl, propyl, β-hydroxyethyl, β-hydroxypropyl and —$CH_2CH_2$(O$CH_2CH_2$)$_p$OH radicals, wherein p is 0 or an integer ranging from 1 to 6, with the proviso that $R_{18}$, $R_{19}$, $R_{20}$ and $R_{21}$ are not simultaneously a hydrogen atom, r and s, which may be identical or different, are integers ranging from 1 to 6, q is 0 or an integer ranging from 1 to 34, $X^-$ is an anion, such as a halide, A is chosen from a dihalide radical and —$CH_2$—$CH_2$—O—$CH_2$—$CH_2$—.

Such compounds are described, for example, in European Patent Application 122 324.

Non-limiting mention may be made, for example, among these, of the products "Mirapol® A 15", "Mirapol® AD1", "Mirapol® AZ1" and "Mirapol® 175", sold by Miranol.

(9) Quaternary polymers of vinylpyrrolidone and of vinylimidazole, for example, the products sold under the names Luviquat® FC 905, FC 550 and FC 370 by BASF.

(10) Crosslinked polymers of methacryloyloxy($C_1$-$C_4$) alkyltri($C_1$-$C_4$)alkylammonium salts, such as the polymers obtained by homopolymerization of dimethylaminoethyl methacrylate quaternized by methyl chloride or by copolymerization of acrylamide with dimethylaminoethyl methacrylate quaternized by methyl chloride, the homo- or copolymerization being followed by a crosslinking by a compound possessing olefinic unsaturation, for example, methylenebisacrylamide.

(11) Polyalkyleneimines, for instance, polyethyleneimines and their derivatives. These polymers are described, for example, in European Patent Application 1 426 035 and International Patent Application WO 2005/092274.

Polyethyleneimines are described, for instance, in the documents: "Kirk-Othmer Encyclopedia of Chemical Technology", 3rd edition, vol. 20, 1982, pp. 214-216, and "Polyethyleneimine Prospective Application", H. N. Feigenbaum, Cosmetics & Toiletries, 108, 1993, p. 73.

In at least one embodiment, the polyethyleneimines (PEI) which can be used may exhibit the following formula:

wherein: n is the mean number of ethyleneimine units ranging from 5 to 10 000.

In at least one embodiment, ethyleneimine homopolymers can be branched.

Non-limiting mention may be made in the context of the present disclosure, for example, of PEI-7 (n=7), PEI-15 (n=15), PEI-30 (n=30), PEI-45 (n=45), PEI-275 (n=275), PEI-700 (n=700), PEI-1000 (n=1000), PEI-1400 (n=1400), PEI-1500 (n=1500), PEI-1750 (n=1750) and PEI-2500 (n=2500).

In at least one embodiment, non-limiting mention may be made of the polyethyleneimines of the Lupasol range, for example, the products sold under the names Lupasol G35, FG, PS, HF and P, and Polymin SK from BASF.

In yet another embodiment, the polyethyleneimines (PEI) can be modified by hydrophilic grafts, for example, polyethylene glycol (PEG), polyvinyl acetate (PVA) or polyacrylate, or by hydrophobic grafts, for example silicone and/or $C_8$-$C_{30}$ carbonaceous fatty chains, as described, for instance, in International Patent Applications WO 97/20879, WO 97/23456, WO 02/095122, and WO 02/15854, and U.S. Pat. No. 5,756, 080 and European Patent 0 524 612 and in the publication H. Petersen et al., Macromolecules, 2002, 35, p. 6867.

PEI-PEG compounds are sold, for example, under the names Lupasol SC61B, SC62J, LU158 and HEO1 by BASF.

PEI compounds comprising fatty chains are sold, for instance, under the names Lupasol ESA 51685 or LU157 by BASF.

12) Polymers derived from amino acids

In at least one embodiment of the present disclosure, the polymers present in the composition can also be chosen from polymers comprising at least 2 units of at least one basic amino acid.

The at least one basic amino acid is chosen, in a non-restrictive manner, from: ornithine, aspargine, glutamine, lysine and arginine. Polymers comprising at least 2 units of at least one basic amino acid that are present in the composition may comprise from 2 to 10 000 basic amino acid units.

Such polymers can be modified by hydrophilic grafts (polyethylene glycol, PVA (polyvinyl acetate) or polyacrylate) or hydrophobic grafts (PDMS (polydimethylsiloxane comprising $C_8$-$C_{30}$ carbonaceous fatty chains)).

Non-limiting mention may be made in the context of the present disclosure of the following publication for the synthesis of polylysine-PEG: G L Kenausis et al., Journal of Physical Chemistry B, 2000, 104, p. 3298.

Non-limiting mention may also be made of International Patent Application WO 00/071601: synthesis of alkoxylated poly(basic amino acid)s, in particular polylysine-polyethylene glycol.

Non-limiting mention may be made of polylysines that are described in Japanese Patent 2003-040724.

In at least one embodiment, non-limiting mention may be made, for example, of the poly-ε-lysine and its silicone derivatives produced by Chisso under the "polylysine" names.

13) Aminated dendrimers

As used herein, "dendrimers comprising primary amines in the terminal position" is understood to mean polymeric compounds composed of a core and of generation of base units, monomers or spindles, onto which an end group T carrying a primary amine functional group has been grafted.

Non-limiting mention may be made, for example, of polyamidoamine dentrimers, such as those sold, for example, under the commercial reference Starburst PAMAM by Dendritech (block copolymers of ethylenediamine and of methyl acrylate) or those sold, for instance, under the commercial reference Astromols (DAB) by DSM.

14) Polyallylamines

Non-limiting examples of polyallylamines, such as those produced by Nitto Boseki Co., and their derivatives, such as those described in International Patent Application WO 2005/092274.

Useful polymers that may be present in the composition, can be chosen according to the present disclosure, from amphoteric polymers chosen from polymers comprising B and C units distributed randomly in the polymer chain, wherein B is a unit derived from a monomer comprising at least one basic nitrogen atom and C is a unit derived from an acidic monomer comprising at least one carboxyl or sulfo groups or alternatively, B and C are groups derived from zwitterionic carboxybetaine or sulfobetaine monomers;

In at least one embodiment, B and C are cationic polymer chains comprising primary, secondary, tertiary or quaternary amine groups, wherein at least one of the amine groups carries a carboxyl or sulfo group connected via a hydrocarbon group, or alternatively, B and C form part of a chain of a polymer comprising an α,β-dicarboxyethylene unit, one of the carboxyl groups of which has been reacted with a polyamine comprising one or more primary or secondary amine groups.

In another embodiment, amphoteric polymers corresponding to the definition given above are chosen from the following polymers:

1) Copolymers comprising acidic vinyl units and comprising basic vinyl units, such as those resulting from the copolymerization of a monomer derived from a vinyl compound carrying a carboxyl group, such as acrylic acid, methacrylic acid, maleic acid or α-chloroacrylic acid, and of a basic monomer derived from a substituted vinyl compound comprising at least one basic atom, such as dialkylaminoalkyl methacrylate and acrylate or dialkylaminoalkylmethacrylamide and -acrylamide. Such compounds are described in U.S. Pat. No. 3,836,537.

2) Polymers comprising units derived:
   a) from at least one monomer chosen from acrylamides and methacrylamides substituted on the nitrogen atom by an alkyl group,
   b) from at least one acidic comonomer comprising at least one reactive carboxyl groups, and
   c) from at least one basic comonomer, such as esters comprising primary, secondary, tertiary and quaternary amine substituents of acrylic and methacrylic acids and the quaternization product of dimethylaminoethyl methacrylate with dimethyl or diethyl sulfate.

In at least one embodiment, N-substituted acrylamides or methacrylamides which comprise $C_2$-$C_{12}$ alkyl groups are used, for example, N-ethylacrylamide, N-tert-butylacrylamide, N-tert-octylacrylamide, N-octylacrylamide, N-decylacrylamide or N-dodecylacrylamide, and the corresponding methacrylamides.

In at least one embodiment, the acidic comonomers are chosen from acrylic, methacrylic, crotonic, itaconic, maleic, fumaric acids and $C_1$-$C_4$ alkyl monoesters, for example, maleic or fumaric acids or anhydrides.

In another embodiment, the basic comonomers are chosen from aminoethyl, butylaminoethyl, N,N-dimethylaminoethyl and N-tert-butylaminoethyl methacrylates.

Other useful copolymers that may be mentioned, in a non-limiting manner, include for which the CTFA name (4th Ed., 1991) is Octylacrylamide/acrylates/butylaminoethyl methacrylate copolymers, such as the products sold under the name Amphomer® or Lovocryl® 47 by National Starch.

(3) Partially or completely acylated and crosslinked polyaminoamides deriving from polyaminoamides of the following formula (II):

$$-\!\!\!+\!CO\!-\!R_{10}\!-\!CO\!-\!Z\!+\!\!\!- \quad (II)$$

wherein: $R_{10}$ is a divalent group derived from a saturated dicarboxylic acid, from an aliphatic mono- or dicarboxylic acid comprising an ethylenic double bond, from an ester of a lower alkanol having 1 to 6 carbon atoms of these acids, or from a group derived from the addition of any one of the acids with a bisprimary or bissecondary amine, and wherein Z is chosen from a group derived from a bisprimary, mono- or bissecondary polyalkylene-polyamine and in one embodiment, may represent:
a) in the proportions of 60 mol % to 100 mol %, the group:

$$-\!\!\!\underset{H}{N}\!\!\!-\!\!\!+\!(CH_2)_x\!-\!\underset{H}{N}\!\!+\!\!\!-_p \quad (IV)$$

wherein x=2 and p=2 or 3, or alternatively, x=3 and p=2; this group may be derived from diethylenetriamine, triethylenetetraamine or dipropylenetriamine;
b) in the proportions of 0 mol % to 40 mol %, the above group (IV), wherein x=2 and p=1 and is derived from ethylenediamine, or the group derived from piperazine:

$$-N\!\!\!\underset{\diagdown}{\diagup}\!\!\!N-$$

c) in the proportions of 0 mol % to 20 mol %, wherein the group —NH—$(CH_2)_6$—NH— is derived from hexamethylenediamine,
wherein these polyaminoamides are crosslinked by addition reaction of a bifunctional crosslinking agent chosen from epihalohydrins, diepoxides, dianhydrides or bisunsaturated derivatives, with a crosslinking agent per amine group of the polyaminoamide, present in an amount ranging from 0.025 mol to 0.35 mol, and acylated by reaction with acrylic acid, chloroacetic acid or an alkanesulfone or their salts thereof.

In at least one embodiment, the saturated carboxylic acids are chosen from acids comprising from 6 to 10 carbon atoms, such as adipic, 2,2,4-trimethyladipic or 2,4,4-trimethyladipic, or terephthalic acids, and the acids comprising an ethylenic double bond, such as, acrylic, methacrylic or itaconic acids.

According to the present disclosure, the alkanesultones used in the acylation may be, for example, propane- or butanesultone and the salts of the acylating agents may be, for instance, the sodium or potassium salts.

(4) Polymers comprising zwitterionic units of formula (IV):

$$R_{11}\!-\!\!\!+\!\!\underset{R_{13}}{\overset{R_{12}}{\underset{|}{\overset{|}{C}}}}\!\!\!+\!\!\!_y\!\!\underset{R_{15}}{\overset{R_{14}}{\underset{|}{\overset{|}{N^+}}}}\!\!\!-\!(CH_2)_z\!-\!\overset{O}{\underset{\|}{C}}\!-\!O^- \quad (IV)$$

wherein:
$R_{11}$ is a polymerizable unsaturated group, such as an acrylate, methacrylate, acrylamide or methacrylamide group;
y and z are integers ranging from 1 to 3;
$R_{12}$ and $R_{13}$, are chosen from a hydrogen atom, a methyl group, an ethyl group and a propyl group; and
$R_{14}$ and $R_{15}$ are chosen from a hydrogen atom and an alkyl group such that the sum of the carbon atoms in $R_{14}$ and $R_{15}$ does not exceed 10.

In at least one embodiment, the polymers comprising such units can also comprise units derived from non-zwitterionic monomers, such as dimethyl- or diethylaminoethyl acrylate or methacrylate or alkyl acrylates or methacrylates, acrylamides or methacrylamides, or vinyl acetate.

Non-limiting mention may be made, for example, of methyl methacrylate/dimethylcarboxymethylammonioethyl methacrylate copolymers, such as the product sold under the name Diaformer Z301 by Sandoz.

(5) Polymers derived from chitosan comprising monomer units corresponding to the following formulae:

(D)

(E)

(F)

wherein: the unit (D) is present in proportions ranging from 0% to 30%, the unit (E) in proportions ranging from 5% and 50% and the unit (F) in proportions ranging from 30% and 90%, it being understood that, in this unit (F), $R_{16}$ is a group of formula:

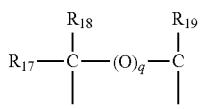

wherein: if q=0, $R_{17}$, $R_{18}$ and $R_{19}$, which may be identical or different, are each chosen from hydrogen, methyl, hydroxyl, acetoxy and amino residues, monoalkylamino and dialkylamino residues, optionally interrupted by at least one nitrogen atom and/or optionally substituted by at least one group chosen from amino, hydroxyl, carboxyl, alkylthio and sulfo groups, and alkylthio residues in which the alkyl group carries an amino residue. In at least one embodiment, at least one of the $R_{17}$, $R_{18}$ and $R_{19}$ groups is a hydrogen atom, or, if q=1, $R_{17}$, $R_{18}$ and $R_{19}$ are chosen from a hydrogen atom, and the acid salts and base salts formed by these compounds.

(6) Polymers corresponding to formula (V) which are, for example, described in French Patent 1 400 366 and are composed of units:

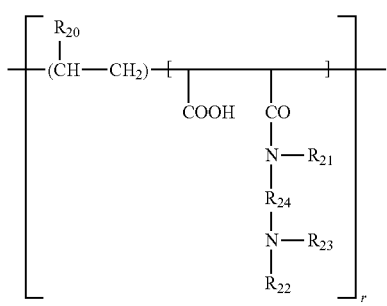

(V)

wherein:

r is an integer greater than or equal to 1, $R_{20}$ is chosen from a hydrogen atom, a $CH_3O$, $CH_3CH_2O$ and a phenyl group;

$R_{21}$ is chosen from a hydrogen atom and a lower alkyl group, such as methyl or ethyl;

$R_{22}$ is chosen from a hydrogen atom and a lower $C_1$-$C_6$ alkyl group, such as methyl or ethyl; and $R_{23}$ is chosen from a lower $C_1$-$C_6$ alkyl group, such as methyl or ethyl, and a group corresponding to the formula: —$R_{24}$—$N(R_{22})_2$, $R_{24}$ is chosen from a —$CH_2$—$CH_2$—, —$CH_2$—$CH_2$—$CH_2$— and —$CH_2$—$CH(CH_3)$— group and $R_{22}$ having the meanings mentioned above.

(7) Polymers derived from the N-carboxyalkylation of chitosan, such as the N-(carboxymethyl)chitosan or the N-(carboxybutyl)chitosan sold under the name "Evalsan" by Jan Dekker.

(8) Amphoteric polymers of the -D-X-D-X— type chosen from:

a) polymers obtained by reaction of chloroacetic acid or sodium chloroacetate with compounds comprising at least one unit of formula (VI):

-D-X-D-X-D- (VI)

wherein D is a group

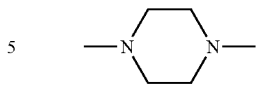

and X is the symbol E or E', E or E', which may be identical or different, and may be a bivalent group which is a straight- or branched-chain alkylene group comprising up to 7 carbon atoms in the main chain which is unsubstituted or substituted by hydroxyl groups and which can optionally comprise oxygen, nitrogen or sulfur atoms or 1 to 3 aromatic and/or heterocyclic rings, wherein the oxygen, nitrogen and sulfur atoms being present in the form of ether, thioether, sulfoxide, sulfone, sulfonium, alkylamine or alkenylamine groups or hydroxyl, benzylamine, amine oxide, quaternary ammonium, amide, imide, alcohol, ester and/or urethane groups.

b) polymers of formula (VI'):

-D-X-D-X- (VI')

wherein D is a group

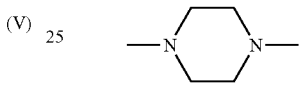

and X is the symbol E or E' and at least once E', E having the meaning indicated above and E' being a bivalent group which is a straight- or branched-chain alkylene group having up to 7 carbon atoms in the main chain which is unsubstituted or substituted by one or more hydroxyl groups and which comprises at least one nitrogen atom, the nitrogen atom being substituted by an alkyl chain optionally interrupted by an oxygen atom and necessarily comprising one or more carboxyl functional groups and at least one hydroxyl functional groups and betainized by reaction with chloroacetic acid or sodium chloroacetate.

(9) ($C_1$-$C_5$)Alkyl vinyl ether/maleic anhydride copolymers partially modified by semiamidation with an N,N-dialkylaminoalkylamine, such as N,N-dimethylaminopropylamine, or by semiesterification with an N,N-dialkylaminoalkanol. These copolymers can also comprise other vinyl comonomers, such as vinylcaprolactam.

Non-limiting mention will be made in at least one embodiment of the present disclosure, among the amphoteric polymers mentioned above, of those of family (3), such as the copolymers with the CTFA name of Octylacrylamide/acrylates/butylaminoethyl methacrylate copolymer, such as the products sold, for example, under the names Amphomer®, Amphomer® LV 71 or Lovocryl® 47 by National Starch, and those of family (4), such as methyl methacrylate/dimethylcarboxymethylammonioethyl methacrylate copolymers, sold, for example, under the name Diaformer Z301 by Sandoz.

Other useful polymers that may be present in the composition can be nonionic polymers, such as:

polyalkyloxazolines;

vinyl acetate homopolymers;

copolymers of vinyl ester (the vinyl group directly connected to the oxygen atom of the ester group and the vinyl ester having a saturated, linear or branched, $C_1$-$C_{19}$ hydrocarbon radical bonded to the carbonyl of the ester group) and of at least one other monomer which can be a vinyl ester (other than the vinyl ester already present), an α-olefin (having from 8 to 28 carbon atoms), an acrylic ester, a maleic ester, an ethylene, an alkyl vinyl ether (the alkyl group of which comprises from 2 to 18 carbon atoms) or an allyl or methallyl ester (having a saturated, linear or branched, $C_2$-$C_{19}$ hydrocarbon radical bonded to the carbonyl of the ester group).

In at least one embodiment of the present disclosure, these copolymers can be partially crosslinked using crosslinking agents which can be either of the vinyl type or of the allyl or methallyl type, such as tetraallyloxyethane, divinylbenzene, divinyl octane-dioate, divinyl dodecanedioate and divinyl octadecanedioate.

Examples of copolymers that may be mentioned include, but are not limited to: vinyl acetate/allyl stearate, vinyl acetate/vinyl laurate, vinyl acetate/vinyl stearate, vinyl acetate/octadecene, vinyl acetate/octadecyl vinyl ether, vinyl propionate/allyl laurate, vinyl propionate/vinyl laurate, vinyl stearate/1-octadecene, vinyl acetate/1-dodecene, vinyl stearate/ethyl vinyl ether, vinyl propionate/cetyl vinyl ether, vinyl stearate/allyl acetate, vinyl 2,2-dimethyloctanoate/vinyl laurate, allyl 2,2-dimethylpentanoate/vinyl laurate, vinyl dimethylpropionate/vinyl stearate, allyl dimethylpropionate/vinyl stearate, vinyl acetate/dibutyl maleate propionate, vinyl acetate/vinyl stearate, crosslinked with 0.2% of divinylbenzene, vinyl dimethylpropionate/vinyl laurate, crosslinked with 0.2% of divinylbenzene, vinyl acetate/octadecyl vinyl ether, crosslinked with 0.2% of tetraallyloxyethane, vinyl acetate/allyl stearate, crosslinked with 0.2% of divinylbenzene, vinyl acetate/1-octadecene, crosslinked with 0.2% of divinylbenzene, and allyl propionate/allyl stearate, crosslinked with 0.2% of divinylbenzene.

homopolymers and copolymers of acrylic esters. In at least one embodiment, the homopolymers and copolymers are obtained from monomers chosen from isooctyl(meth)acrylate, isononyl(meth)acrylate, 2-ethylhexyl(meth)acrylate, lauryl (meth)acrylate, isopentyl(meth)acrylate, n-butyl (meth)acrylate, isobutyl(meth)acrylate, methyl(meth)acrylate, tert-butyl(meth)acrylate, tridecyl(meth)acrylate, stearyl (meth)acrylate and mixtures of these. Non-limiting mention will be made, for example, of the alkyl acrylate/cycloalkyl acrylate copolymer sold by Phoenix Chem. under the name Giovarez AC-5099 mL or copolymers of alkyl acrylates and of alkyl methacrylates, such as the products provided by Röhm & Haas under the names Primal® AC-261 K and Eudragit® NE 30 D, by BASF under the name 8845 or by Hoechst under the name Appretan® N9212;

copolymers of acrylonitrile and of a nonionic monomer chosen, for example, from butadiene and alkyl(meth)acrylates, or further for example, the products provided under the name CJ 0601 B by Röhm & Haas;

styrene homopolymers;

copolymers of styrene or styrene derivatives, for example, methylstyrene, chlorostyrene or chloromethylstyrene. In at least one embodiment of the present disclosure, the copolymer comprising at least one styrene block can be a diblock, triblock or multiblock copolymer of star or radial form. The copolymer comprising at least one styrene block can additionally comprise, for example, an alkylstyrene (AS) block, an ethylene/butylene (EB) block, an ethylene/propylene (EP) block, a butadiene (B) block, an isoprene (I) block, an acrylate (A) block, a methacrylate (MA) block or combinations thereof. The copolymer comprising at least one block composed of styrene units or units derived from styrene can be a diblock or triblock copolymer, for example, polystyrene/polyisoprene or polystyrene/polybutadiene, such as those sold or manufactured under the name "Luvitol HSB" by BASF, and polystyrene/copoly(ethylene/propylene) or polystyrene/copoly(ethyl/butylene), such as those sold or manufactured, for example, under the trade name "Kraton" by Shell Chemical Co. or Gelled Permethyl 99A by Penreco, can be used.

Non-limiting mention may be made in the context of the disclosure of Kraton G1650 (SEBS), Kraton G1651 (SEBS), Kraton G1652 (SEBS), Kraton G1657X (SEBS), Kraton G1701X (SEP), Kraton G1702X (SEP), Kraton G1726X (SEB), Kraton D-1101 (SBS), Kraton D-1102 (SBS), Kraton D-1107 (SIS), Gelled Permethyl 99A-750, Gelled Permethyl 99A-753-58 (blend of star block polymer and of triblock polymer), Gelled Permethyl 99A-753-59 (blend of star block polymer and of triblock polymer), Versagel 5970 and Versagel 5960 from Penreco (blend of star polymer and of triblock polymer in isododecane).

Styrene/methacrylate copolymers can also be used according to the present disclosure and may be mentioned, in a non-limiting manner as the polymers sold under the references OS 129880, OS 129881 and OS 84383 by Lubrizol (styrene/methacrylate copolymer). Non-limiting mention may also be made of copolymers of styrene and of alkyl (meth)acrylate, such as the products Mowilith® LDM 6911, Mowilith® DM 611 and Mowilith® LDM 6070 provided by Hoechst, or the products Rhodopas® SD 215 and Rhodopas® DS 910 provided by Rhône-Poulenc.

polyamides;

vinyllactam homopolymers other than vinylpyrrolidone homopolymers, such as the polyvinylcaprolactam sold, for instance, under the name Luviskol® Plus by BASF;

vinyllactam copolymers, such as a poly(vinylpyrrolidone/vinyllactam) copolymer sold under the trade name Luvitec® VPC 55K65W by BASF, poly(vinylpyrrolidone/vinyl acetate) copolymers, such as those sold, for example, under the name PVPVA® S630L by ISP or Luviskol® VA 73, VA 64, VA 55, VA 37 and VA 28 by BASF, and poly(vinylpyrrolidone/vinyl acetate/vinyl propionate) terpolymers, such as that sold under the name Luviskol® VAP 343 by BASF.

vinylpyrrolidone copolymers, such as copolymers of a $C_2$ to $C_{30}$ alkene, such as a $C_3$ to $C_{22}$ alkene, and combinations thereof. Non-limiting mention may be made, as examples of VP copolymers which can be used in the present disclosure, of VP/vinyl laurate copolymer, VP/vinyl stearate copolymer, butylated polyvinylpyrrolidine (PVP), VP/hexadecane copolymer, VP/eicosene copolymer, VP/tricontene copolymer, or VP/acrylic acid/lauryl methacrylate copolymer. Such copolymers are, for example, those sold by ISP under the name Ganex V 220 or Ganex V 216.

polymers carrying fluorinated groups, for example, polyperfluoroethers, such as the Fomblin products described in U.S. Pat. No. 5,948,393, or the alkyl (meth)acrylate/perfluoroalkyl(meth)acrylate copolymers described in European Patent Application 0 815 836 and U.S. Pat. No. 5,849,318.

nonionic polyurethanes that can be nonassociative or associative.

As used herein, "nonassociative polyurethane" is understood to mean polycondensates comprising at least one polyurethane block and not comprising, in their structure, a terminal or pendant alkyl or alkenyl chain, comprising more than 10 carbon atoms. They are described, for example, in European Patent Applications 0 751 162, 0 637 600, 0 648 485, 0 656 021, and 0 619 111 and French Patent 2 743 297 and International Patent Application WO 94/03510 of BASF.

The nonassociative polyurethanes that may be used in accordance with the present disclosure can be soluble in the cosmetically acceptable aqueous medium or form a dispersion in this medium. The dispersion can then comprise at least 0.05% of surfactant to keep the nonassociative polyurethane dispersed.

According to at least one embodiment of the present disclosure, any type of surfactant can be used in the dispersion. In at least one embodiment, the surfactant is nonionic. The mean size of the particles of the nonassociative polyurethane in the dispersion ranges, for example, from 0.1 to 1 micrometer.

In at least one embodiment, the nonassociative polyurethane can be formed of an arrangement of blocks obtained in the following from:

(1) at least one compound which comprises at least two active hydrogen atoms per molecule;
(2) at least one diol or a mixture of diols comprising acid functional groups or their salts; and
(3) at least one di- or polyisocyanate.

It may be beneficial in the context of the present disclosure for the compounds (1) to be chosen from diols, diamines, polyesterols, polyetherols and their mixtures.

Non-limiting examples of compounds (I) useful in the present disclosure are linear polyethylene glycols and polypropylene glycols, for instance, those which are obtained by reaction of ethylene or propylene oxide with water or diethylene or dipropylene glycol in the presence of sodium hydroxide as a catalyst. Such polyalkylene glycols generally have a molecular weight of ranging from 600 to 20 000.

Other useful organic compounds include, but are not limited to mercapto, amino, carboxyl and hydroxyl groups. Non-limiting mention may be made of polyhydroxylated compounds, such as polyether diols, polyester diols, polyacetal diols, polyamide diols, polyester polyamide diols, poly(alkylene ether) diols, polythioether diols and polycarbonate diols.

In at least one embodiment, the polyether diols are, for example, the condensation products of ethylene oxide, of propylene oxide or of tetrahydrofuran, their copolymerization or condensation products, which are grafted or block products, such as mixtures of condensates of ethylene oxide and of propylene oxide, and products of the polymerization of olefins under high pressure, with alkylene oxide condensates. Suitable polyether diols as disclosed herein, are, for example, prepared by condensation of alkylene oxides and of polyhydric alcohols, such as ethylene glycol, 1,2-propylene glycol and 1,4-butanediol.

The polyester diols, polyesteramides and polyamide diols according to at least one embodiment of the present disclosure, may be saturated and are obtained, for example, from the reaction of saturated or unsaturated polycarboxylic acids with polyhydric alcohols, diamines or polyamines. Use may be made, to prepare these compounds, for example, of adipic acid, succinic acid, phthalic acid, terephthalic acid and maleic acid. Suitable polyhydric alcohols for preparing the polyesters include but are not limited to, for example, ethylene glycol, 1,2-propylene glycol, 1,4-butanediol, neopentyl glycol and hexanediol. Use may also be made of aminoalcohols, for example ethanolamine. Suitable diamines for preparing polyesteramides are, for instance, ethylenediamine and hexamethylenediamine.

Suitable polyacetals, according to the present disclosure, can be prepared, for example, from 1,4-butanediol or hexanediol and formaldehyde. Suitable polythioethers can be prepared, for example, by a condensation reaction between thioglycols, alone or in combination with other glycols, such as ethylene glycol or 1,2-propylene glycol, or with other polyhydroxylated compounds. In at least one embodiment, polyhydroxylated compounds already comprising urethane groups, natural polyols, which can be further modified, for example castor oil and carbohydrates, can also be used.

In at least one embodiment, the compound of group (1) is a polyesterol, for example, a polyester diol formed by the reaction of at least one (di)polyol (1a) and of at least one acid (1b). The (di)polyol (1a) is chosen, for instance, from neopentyl glycol, 1,4-butanediol, hexanediol, ethylene glycol, diethylene glycol, propylene glycol, butylene glycol, neopentyl glycol and (di)polyethylene glycol. The acid (1b) is chosen, for example, from phthalic acid, isophthalic acid, adipic acid and (poly)lactic acid.

Compound (2) may be useful according to the present disclosure, for example, hydroxycarboxylic acid, such as dimethylolpropanoic acid (DMPA), or a 2,2-dihydroxymethylcarboxylic acid. In at least one embodiment, the compound (2) is used as coupling block. In at least another embodiment, compounds (2), comprising at least one poly($\alpha,\alpha$-dihydroxylated carboxylic acid) may be used.

Other useful compounds (2) which may be used in accordance with the present disclosure may include, but are not limited to 2,2-di(hydroxymethyl)acetic acid, 2,2-dihydroxymethylpropionic acid, 2,2-dihydroxymethylbutyric acid and 2,2-dihydroxymethylpentanoic acid.

Examples of the di- or polyisocyanate (3) may include, but are not limited to hexamethylene diisocyanate, isophorone diisocyanate (IDPI), toluoylene diisocyanate, 4,4'-diphenylmethane diisocyanate (DPMD) and 4,4'-dicyclohexylmethane diisocyanate (DCMD), methylenedi-p-phenyl diisocyanate, methylenebis(4-cyclohexylisocyanate), toluene diisocyanates, 1,5-naphthalene diisocyanate, 4,4'-diphenylmethane diisocyanate, 2,2'-dimethyl-4,4'-diphenylmethane diisocyanate, 1,3-phenylene diisocyanate, 1,4-phenylene diisocyanate, mixtures of 2,4- and of 2,6-toluene diisocyanates, 2,2'-dichloro-4,4'-diisocyanatodiphenylmethane, 2,4-dibromo-1,5-diisocyanatonaphthalene, 1,4-butane diisocyanate, 1,6-hexane diisocyanate and 1,4-cyclohexane diisocyanate.

In at least one embodiment, the nonassociative polyurethane can be formed using an additional compound (4) which generally serves to extend its chain. These compounds (4) can be chosen from the group of saturated or unsaturated glycols, such as ethylene glycol, diethylene glycol, neopentyl glycol or triethylene glycol; amino alcohols, such as ethanolamine, propanolamine or butanolamine; heterocyclic, aromatic, cycloaliphatic and aliphatic primary amines; diamines; carboxylic acids, such as aliphatic, aromatic and heterocyclic carboxylic acids, for example oxalic, succinic, glutaric, adipic, sebacic and terephthalic acids; and aminocarboxylic acids. In at least one embodiment, the compounds (4) are aliphatic diols.

Useful nonassociative polyurethanes that may be used according to the present disclosure can also be further formed from additional compounds (5) having a silicone backbone, such as polysiloxanes, polyalkylsiloxanes or polyarylsiloxanes, for example, polyethylsiloxanes, polymethylsiloxanes and polyphenylsiloxanes, optionally comprising hydrocarbon chains grafted to the silicon atoms.

In at least one embodiment, the nonassociative polyurethanes used may comprise a base repeating unit corresponding to formula (VI):

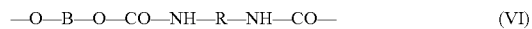
—O—B—O—CO—NH—R—NH—CO—    (VI)

wherein:

B is a divalent $C_1$ to $C_{30}$ hydrocarbon group, optionally substituted by a group comprising at least one carboxylic acid functional group and/or one or more sulfonic acid functional groups, wherein the carboxylic and/or sulfonic acid functional groups are in the free form or alternatively, partially or completely neutralized by an inorganic or organic base, and R is a divalent group chosen from aliphatic $C_1$ to $C_{20}$ hydrocarbon groups, cycloaliphatic $C_3$ to $C_{20}$ hydrocarbon groups and aromatic $C_6$ to $C_{20}$ hydrocarbon groups, such as, $C_1$ to $C_{20}$ alkylene groups, $C_6$ to $C_{20}$ arylene groups, $C_3$ to $C_{20}$ cycloalkylene groups, or combinations thereof, wherein these groups may or may not be substituted.

The R group may be chosen from the groups corresponding to the following formulae:

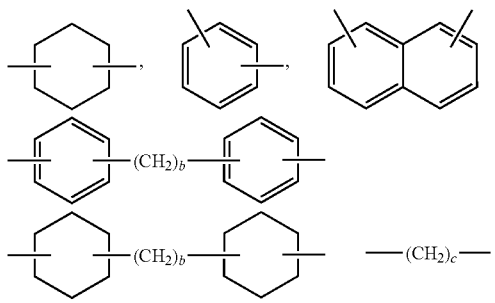

wherein: b is an integer ranging from 0 to 3 and c is an integer ranging from 1 to 20, for example, ranging from 2 to 12.

In at least one embodiment of the present disclosure, the R group is chosen from hexamethylene, 4,4'-biphenylenemethane, 2,4- and/or 2,6-tolylene, 1,5-naphthylene, p-phenylene and methylene-4,4-biscyclohexyl and the divalent group derived from isophorone.

Nonassociative polyurethane that may be used in the present disclosure can comprise, in addition, at least one polysiloxane sequence, the base repeating unit of which corresponds, for example, to formula (VII):

$$—O—P—O—CO—NH—R—NH—CO— \quad \text{(VII)}$$

wherein:

P is a polysiloxane segment, and

R is a divalent group chosen from aliphatic $C_1$ to $C_{20}$ hydrocarbon groups, cycloaliphatic $C_3$ to $C_{20}$ hydrocarbon groups and aromatic $C_6$ to $C_{20}$ hydrocarbon groups, such as, $C_1$ to $C_{20}$ alkylene groups, $C_6$ to $C_{20}$ arylene groups, $C_3$ to $C_{20}$ cycloalkylene groups or combinations thereof, wherein these groups may or may not be substituted.

In at least one embodiment, the polysiloxane segment P corresponds to formula (VIII) below:

wherein:

the A groups, which can be identical or different, are chosen from monovalent $C_1$ to $C_{20}$ hydrocarbon groups devoid of ethylenic unsaturation and from aromatic groups, Y is a divalent hydrocarbon group, and z is an integer chosen so that the weight-average molecular weight of the polysiloxane segment ranges from 300 and 10 000.

In at least one embodiment, the divalent group Y is chosen from alkylene groups of formula —$(CH_2)_a$— wherein a is an integer which can range from 1 to 10.

The groups A can be chosen from $C_{1-8}$ alkyl groups, for example, methyl, ethyl, propyl, isopropyl, butyl, pentyl, hexyl and octyl groups; $C_{3-8}$ cycloalkyl groups, for instance, the cyclohexyl group; $C_{6-10}$ aryl groups, for example, phenyl; $C_{7-10}$ arylalkyl groups, for example, benzyl and phenylethyl, and also tolyl and xylyl groups.

Non-limiting mention may be made, as non-limiting examples of nonassociative polyurethane, of the dimethylolpropionic acid/isophorone diisocyanate/neopentyl glycol/polyesterdiols copolymer (also known under the name of polyurethane-1, INCI name) sold, for example, under the trade name Luviset® PUR by BASF and the dimethylolpropionic acid/isophorone diisocyanate/neopentyl glycol/polyesterdiols/silicone diamine copolymer (also known under the name of polyurethane-6, INCI name) sold, for instance, under the trade name Luviset® Si PUR A by BASF.

Such polyurethanes are present in the composition according to the present disclosure in the non-neutralized and thus nonionic form.

As used herein, "associated polyurethane" is understood to mean a polyurethane having at least one end or pendent alkyl chain comprising at least 10 carbon atoms. This type of polymer is capable of interacting with itself or with specific compounds, such as surfactants, to result in thickening of the medium.

Non-limiting mention may be made, by way of example of nonionic associative polyurethane, of a water-soluble or water-swellable acrylic copolymer which comprises:

a) 40% to 99.5% by weight, for example, 30% to 65% by weight, of a nonsurfactant monomer comprising monoethylenic unsaturation and b) 0.5% to 60% by weight, for instance, 10% to 50% by weight, of a nonionic urethane monomer which is the reaction product of a monohydric nonionic surfactant with a monoisocyanate comprising monoethylenic unsaturation.

According to the present disclosure, the copolymer must comprise a significant proportion, as indicated above, of a monomer a) comprising monoethylenic unsaturation which does not have surfactant properties. Non-limiting examples of monomers which give water-insoluble polymers when they are homopolymerized include, but are not limited to $C_1$-$C_4$ alkyl acrylates and methacrylates, such as methyl acrylate, ethyl acrylate, butyl acrylate and the corresponding methacrylates. In at least one embodiment, the monomers are methyl and ethyl(meth)acrylates. Other useful monomers which can be used herein may include, but are not limited to styrene, vinyltoluene, vinyl acetate, acrylonitrile and vinylidene chloride. In at least one embodiment, unreacted monomers are used, these monomers being those in which the sole ethylenic group is the only group which is reactive under the conditions of the polymerization. However, monomers which comprise groups which are reactive under the action of heat can be used in some situations, such as hydroxyethyl acrylate.

The monohydric nonionic surfactants used to obtain the nonionic urethane monomer b) are well known in the art and are generally alkoxylated hydrophobic compounds comprising an alkylene oxide forming the hydrophilic part of the molecule. The hydrophobic compounds are generally composed of an aliphatic alcohol or an alkylphenol wherein a carbon chain comprising at least six carbon atoms constitutes the hydrophobic part of the surfactant.

In at least one embodiment of the present disclosure, the monohydric nonionic surfactants have the formula:

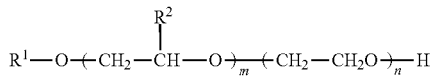

wherein:

R$^1$ is chosen from a C$_6$-C$_{30}$ alkyl and C$_8$-C$_{30}$ aralkyl group;

R$^2$ is a C$_1$-C$_4$ alkyl group;

n is a mean number ranging from 5 to 150; and m is a mean number ranging from 0 to 50, provided that n is at least as great as m and that n+m=5-150.

Non-limiting mention may be made, as C$_6$-C$_{30}$ alkyl groups used in at least one embodiment, of dodecyl and C$_{18}$-C$_{26}$ alkyl radicals. As useful aralkyl groups, non-limiting mention may be made of alkylphenyl groups where the alkyl is a C$_8$-C$_{13}$ alkyl. In at least one embodiment, R$^2$ group is a methyl group.

The monoisocyanate comprising monoethylenic unsaturation used to form the nonionic urethane monomer b) can be chosen from highly varied compounds. In at least one embodiment, use may be made of a compound comprising any copolymerizable unsaturation, such as an acrylic or methacrylic unsaturation or of an allylic unsaturation conferred by allyl alcohol. In at least one embodiment, the monoethylenic monoisocyanates are α,α-dimethyl-m-isopropenylbenzyl isocyanate and methylstyreneisopropyl isocyanate.

The acrylic copolymer defined above is obtained by copolymerization in aqueous emulsion of the components a) and b), which is conventional and described in European Patent Application 0 173 109.

The nonionic associative polyurethanes that may be used in the present disclosure are, for example, polyether polyurethanes comprising, in their chain, both hydrophilic sequences of generally polyoxyethylene nature and hydrophobic sequences which can be aliphatic linkages alone and/or cycloaliphatic and/or aromatic linkages.

In at least one embodiment of the present disclosure, the polyether polyurethanes may comprise at least two lipophilic C$_6$-C$_{30}$ hydrocarbon chains which are separated by a hydrophilic sequence, it being possible for the hydrocarbon chains to be pendent chains or chains at the end of the hydrophilic sequence. In one embodiment, it is possible for one or more pendent chains to be provided. In another embodiment, the polymer can comprise a hydrocarbon chain at one end or at both ends of a hydrophilic sequence.

In at least one embodiment, the polyether polyurethanes can be polysequential, for example, in the triblock form. The hydrophobic sequences can be at each end of the chain, for example: triblock copolymer comprising a central hydrophilic sequence or distributed both at the ends and in the chain, for example, polysequential copolymer. Such polymers can also be graft polymers or star polymers.

In another embodiment, the nonionic polyether polyurethanes comprising a fatty chain can be triblock copolymers, the hydrophilic sequence of which is a polyoxyethoxyl chain comprising from 50 to 1000 ethoxyl groups. The nonionic polyether polyurethanes may comprise a urethane bond between the hydrophilic sequences, hence the origin of the name.

Accordingly, the nonionic polyether polyurethanes comprising a fatty chain may also include hydrophilic sequences of which are bonded to the lipophilic sequences via other chemical bonds.

Non-limiting mention may also be made, as examples of nonionic polyether polyurethanes comprising a fatty chain which can be used in the present disclosure, of Rheolate 205 comprising a urea functional group sold, for example, by Rheox or Rholates 208, 204 or 212, and also Acrysol® 184.

According to the disclosure, mention may also be made, in a non-restrictive manner, of the product Elfacos T210 comprising a C$_{12-14}$ alkyl chain and the product Elfacose T212 comprising a C$_{18}$ alkyl chain from Akzo.

In at least one embodiment, the product DW 1206B from Röhm & Haas comprising a C$_{20}$ alkyl chain and comprising a urethane bond, provided at a dry matter content of 20% in water, can also be used.

Use may also be made of solutions or dispersions of these polymers, such as in water or in an aqueous/alcoholic medium. Non-limiting mention may be made, as examples of such polymers, of Rheolate® 255, Rheolate® 278 and Rheolate® 244, sold by Rheox, and the products DW 1206F and DW 1206J provided by Röhm & Haas.

As disclosed herein, the polyether polyurethanes which can be used are, for example, those described in the paper by G. Formum, J. Bakke and Fk. Hansen, Colloid Polym. Sci., 271, 380-389 (1993).

Examples of nonionic associative polyurethane that may be mentioned in the present disclosure, include, but are not limited to the polyether polyurethanes capable of being obtained by polycondensation of at least three compounds comprising (i) at least one polyethylene glycol comprising from 150 to 180 mol of ethylene oxide, (ii) stearyl alcohol or decyl alcohol and (iii) at least one diisocyanate.

Such polyether polyurethanes are sold, for example, by Röhm & Haas under the names Aculyn® 46 and Aculyn® 44. Aculyn® 46 is a polycondensate of polyethylene glycol comprising 150 or 180 mol of ethylene oxide, of stearyl alcohol and of methylenebis(4-cyclohexyl isocyanate) (SMDI), at 15% by weight in a matrix of maltodextrin (4%) and of water (81%); Aculyn® 44 is a polycondensate of polyethylene glycol comprising 150 or 180 mol of ethylene oxide, of decyl alcohol and of methylenebis(4-cyclohexyl isocyanate) (SMDI), at 35% by weight in a mixture of propylene glycol (39%) and of water (26%).

In at least one embodiment, the alkyl groups of the nonionic polymers mentioned above comprise from 1 to 6 carbon atoms.

According to another embodiment, the polymer is chosen from anionic, nonionic and amphoteric polymers which are, for example, film-forming and/or gelling.

As used herein, "film-forming" polymer is understood to mean a polymer capable of forming, alone or in the presence of an additional agent which is able to form a film, a macroscopically continuous film on a support, for instance, on keratinous substances, such as a cohesive film or a film having a cohesion and mechanical properties such that the film can be isolated from the support.

The compositions in accordance with the present disclosure can also comprise at least one agent commonly used in cosmetics chosen, for example, from reducing agents, fatty substances, plasticizing agents, softening agents, antifoaming agents, moisturizing agents, UV screening agents, inorganic colloids, peptizing agents, solubilizing agents, fragrances, anionic, cationic, nonionic or amphoteric surfactants, proteins, vitamins, oxidation dyes, pearlescent agents, propellants and inorganic or organic thickening agents, such as benzylidenesorbitol and N-acylamino acids, waxes which may or may not be oxyethylenated, paraffins, C$_{10}$-C$_{30}$ fatty acids, such as stearic acid or lauric acid, or C$_{10}$-C$_{30}$ fatty amides, such as lauric acid diethanolamide.

The above additives may be present in the composition in an amount ranging from 0.01% to 20% by weight, relative to the weight of the composition.

A person skilled in the art will take care to choose this or these optional additives so that the beneficial properties intrinsically attached to the formation of the coating in accordance with the invention are not, or not substantially, detrimentally affected.

The composition according to the present disclosure may be in the form of a cream, mousse, stick, dispersion of vesicles, for example, of ionic or nonionic lipids, two-phase or multiphase lotion, spray, aerosol, for example, lacquers, powder or paste.

In at least one embodiment, the composition can be an anhydrous composition, ranging from 0% to 2% by weight of water, such as less than 0.5% of water, or devoid of water, the water not being added during the preparation of the composition but corresponding to the residual water contributed by the ingredients mixed.

As disclosed herein, the composition described above can be employed on dry or wet hair. After application of the composition of the invention, with or without additives as described above, the hair is dried under a hood dryer or using a hair dryer. The additives present can be applied to the hair separately or simultaneously with the composition of the present disclosure.

It is possible to subsequently wash the hair, this washing operation not being essential.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in its respective testing measurement.

The examples that follow are intended to illustrate the invention without being limiting in nature.

EXAMPLES

Example 1

The following composition was produced:

| | |
|---|---|
| Isopropanol | 70 g |
| Cyclopentadimethylsiloxane, sold by Dow Corning under the name of DC245 Fluid | 20 g |
| Dimethylpolysiloxane/urea copolymer, sold under the reference Wacker-Belsil ® UD 60 by Wacker | 10 g |

0.2 g of the composition was applied to a lock weighing 1 g of clean and dry hair. After a leave-in time of 2 minutes, the lock was dried with a hairdryer for 2 minutes. A lock was obtained, the hairs of which were separated and coated. This coating was resistant to shampooing.

Example 2

The following composition was produced:

| | |
|---|---|
| Isopropanol | 67 g |
| Cyclopentadimethylsiloxane, sold by Dow Corning under the name of DC245 Fluid | 20 g |
| Polydimethylsiloxane, sold by Dow Corning under the reference Dow Corning 200 Fluid 60000 cs | 3 g |
| Dimethylpolysiloxane/urea copolymer, sold under the reference Wacker-Belsil ® UD 60 by Wacker | 10 g |

0.2 g of the composition was applied to a lock weighing 1 g of clean and dry hair. After a leave-in time of 2 minutes, the lock was dried with a hairdryer for 2 minutes. A lock was obtained, the hairs of which were separated and coated. This coating was resistant to shampooing.

Example 3

The following composition was produced:

| | |
|---|---|
| Isopropanol | 50 g |
| Cyclopentadimethylsiloxane, sold by Dow Corning under the name of DC245 Fluid | 39 g |
| Aerosil 200 silica | 1 g |
| Dimethylpolysiloxane/urea copolymer, sold under the reference Wacker-Belsil ® UD 60 by Wacker | 10 g |

0.2 g of the composition was applied to a lock weighing 1 g of clean and dry hair. After a leave-in time of 2 minutes, the lock was dried with a hairdryer for 2 minutes. A lock was obtained, the hairs of which were separated and coated. This coating was resistant to shampooing.

Example 4

Composition A was produced:

| | |
|---|---|
| Acrylic acid/ethyl acrylate/N-tert-butylacrylamide terpolymer, Ultrahold Strong ®, sold by BASF | 5 g |
| Water | 95 g |

Composition B was produced:

| | |
|---|---|
| Isopropanol | 50 g |
| Cyclopentadimethylsiloxane, sold by Dow Corning under the name of DC245 Fluid | 40 g |
| Dimethylpolysiloxane/urea copolymer, sold under the reference Wacker-Belsil ® UD 60 by Wacker | 10 g |

0.3 g of composition A was applied to a lock weighing 1 g of clean and wet hair. 0.2 g of composition B was subsequently applied to this lock. After a leave-in time of 2 minutes, the lock was dried with a hairdryer for 2 minutes. A lock was obtained, the hairs of which were separated and coated. This coating was resistant to shampooing.

Example 5

The following composition was produced:

| | |
|---|---|
| Isopropanol | 67 g |
| Cyclopentadimethylsiloxane, sold by Dow Corning under the name of DC245 Fluid | 20 g |
| Polydimethylsiloxane, sold by Dow Corning under the reference Dow Corning 200 Fluid 60000 cs | 3 g |
| Dimethylpolysiloxane/urea copolymer, sold under the reference Wacker-Belsil ® UD 140 by Wacker | 10 g |

0.2 g of the composition was applied to a lock weighing 1 g of clean and dry hair. After a leave-in time of 2 minutes, the lock was dried with a hairdryer for 2 minutes. A lock was obtained, the hairs of which were separate and coated. This coating was resistant to shampooing.

What is claimed is:

1. A method for treating keratinous fibers, comprising applying to said keratinous fibers an anhydrous cosmetic composition comprising at least one nonionic polysiloxane/polyurea block copolymer of formula (I):

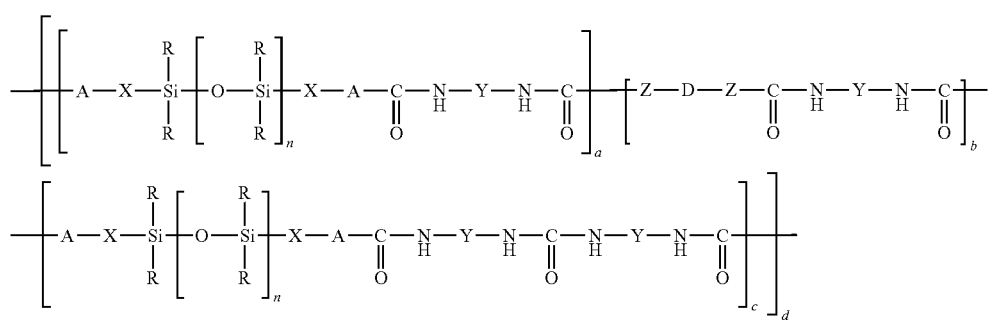

wherein:
R is a monovalent $C_1$-$C_{20}$ hydrocarbon radical, optionally substituted by at least one atom chosen from fluorine and chlorine atoms,
X is a $C_1$-$C_{20}$ alkylene radical, in which nonneighboring methylene units can be replaced by —O— radicals,
A is chosen from an oxygen atom and an amino radical —NR'—,
Z is chosen from an oxygen atom and an amino radical —NR'—,
R' is chosen from a hydrogen atom and a $C_1$-$C_{10}$ alkyl radical,
Y is a divalent $C_1$-$C_{20}$ hydrocarbon radical, optionally substituted with fluorine or chlorine,
D is chosen from a $C_1$-$C_{700}$ alkylene radical, optionally substituted with a group chosen from fluorine, chlorine, $C_1$-$C_6$ alkyl and $C_1$-$C_6$ alkyl ester, in which nonneighboring methylene units can be replaced by —O—, —COO—, —OCO— or —OCOO— radicals,
n is a number ranging from 1 to 4000,
a is a number of at least 1,
b is a number ranging from 0 to 40,
c is a number ranging from 0 to 30, and
d is a number greater than 0,
wherein in at least one embodiment, A is, in at least one of the units (a), an NH radical.

2. A method according to claim 1, wherein said keratinous fibers are hair.

3. A method according to claim 1, wherein the at least one nonionic polysiloxane/polyurea block copolymer comprises at least one polyurethane block.

4. A method according to claim 1, wherein the at least one nonionic polysiloxane/polyurea block copolymer comprises solely polysiloxane blocks and polyurea blocks.

5. A method according to claim 1, wherein the polysiloxane block of the at least one nonionic polysiloxane/polyurea block copolymer comprises polysiloxane in an amount by weight of greater than 5%, relative to the total weight of the copolymer.

6. A method according to claim 5, wherein the amount of polysiloxane in the at least one nonionic polysiloxane/polyurea block copolymer is greater than 90% by weight, relative to the total weight of the copolymer.

7. A method according to claim 1, wherein, in the formula (I), R is methyl.

8. A method according to claim 1, wherein, in the formula (I), X is propylene.

9. A method according to claim 1, wherein, in the formula (I), Z is chosen from an amino radical and an oxygen atom.

10. A method according to claim 1, wherein, in the formula (I), Y is chosen from an aralkylene radical and a linear or cyclic alkylene radical.

11. A method according to claim 1, wherein, in the formula (I), A is an —NH— radical in all the units (a).

12. A method according to claim 11, wherein A is NH in all the units (a), (b), and (c).

13. A method according to claim 1, wherein said at least one nonionic polysiloxane/polyurea block copolymer is obtained by a process which comprises the following two stages:
in the first stage, reacting a cyclic silazane of formula (2) or (2')

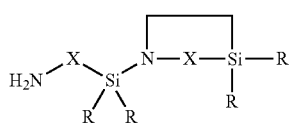

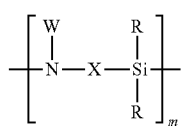

with an organic silicon compound of formula (3):

$$(HO)(R_2SiO)_{n-1}[H] \quad (3)$$

to give an aminoalkylpolydiorganosiloxane of formula (4):

$$H_2N-X-[SiR_2O]_n SiR_2-X-NH_2 \quad (4)$$

and, in a second stage, polymerizing the aminoalkylpolydiorganosiloxane of formula (4) with a diisocyanate of formula (5):

$$OCN-Y-NCO \quad (5)$$

wherein, in the above formulas,

X is a $C_1$-$C_{20}$ alkylene radical, in which nonneighboring methylene units can be replaced by —O— radicals, R is a monovalent $C_1$-$C_{20}$ hydrocarbon radical, optionally substituted by at least one atom chosen from fluorine and chlorine atoms, Y is a divalent $C_1$-$C_{20}$ hydrocarbon radical, optionally substituted with fluorine or chlorine, n is a number ranging from 1 to 4000, m is a number ranging from 1 to 4000, and W is chosen from a hydrogen atom, a substituted or unsubstituted hydrocarbon radical and an $R_2Si$—X—$NH_2$ radical.

14. A method according to claim 1, wherein the at least one nonionic polysiloxane/polyurea block copolymer is a polyureadimethicone.

* * * * *